(12) United States Patent
Mehrling

(10) Patent No.: US 9,993,482 B2
(45) Date of Patent: Jun. 12, 2018

(54) PHARMACEUTICAL COMBINATION COMPRISING A CLASS III RECEPTOR TYROSINE KINASE INHIBITOR AND THE ALKYLATING HISTONE-DEACETYLASE INHIBITOR FUSION MOLECULE EDO-S101 TOGETHER WITH ITS USE IN THE TREATMENT OF CANCER

(71) Applicant: Purdue Pharmaceutical Products L.P., Stamford, CT (US)

(72) Inventor: Thomas Jorg Mehrling, Basel (CH)

(73) Assignee: Purdue Pharmaceutical Products L.P., Stamford, CT (US)

( * ) Notice: Subject to any disclaimer, the term of this patent is extended or adjusted under 35 U.S.C. 154(b) by 0 days. days.

(21) Appl. No.: 15/314,167

(22) PCT Filed: May 26, 2015

(86) PCT No.: PCT/EP2015/061569
§ 371 (c)(1),
(2) Date: Nov. 28, 2016

(87) PCT Pub. No.: WO2015/181154
PCT Pub. Date: Dec. 3, 2015

(65) Prior Publication Data
US 2017/0095482 A1    Apr. 6, 2017

(30) Foreign Application Priority Data
May 28, 2014 (GB) .................................. 1409488.2

(51) Int. Cl.
*A61K 31/5377* (2006.01)
*A61K 31/4184* (2006.01)

(52) U.S. Cl.
CPC ...... *A61K 31/5377* (2013.01); *A61K 31/4184* (2013.01)

(58) Field of Classification Search
CPC .................. A61K 31/5377; A61K 31/4184
See application file for complete search history.

(56) References Cited

U.S. PATENT DOCUMENTS

| | | |
|---|---|---|
| 4,522,811 A | 6/1985 | Eppstein et al. |
| 5,134,127 A | 7/1992 | Stella et al. |
| 5,376,645 A | 12/1994 | Stella et al. |
| 5,571,534 A | 11/1996 | Jalonen et al. |
| 5,874,418 A | 2/1999 | Stella et al. |
| 6,046,177 A | 4/2000 | Stella et al. |
| 6,087,367 A | 7/2000 | Breslow et al. |
| 6,133,248 A | 10/2000 | Stella |
| 6,214,852 B1 | 4/2001 | Kim et al. |
| 6,407,079 B1 | 6/2002 | Muller et al. |
| 8,609,864 B2 | 12/2013 | Chen et al. |
| 8,962,855 B2 | 2/2015 | Chen et al. |
| 9,096,627 B2 | 8/2015 | Chen et al. |
| 9,376,395 B2 * | 6/2016 | Chen ........................ A61K 31/16 |
| RE46,144 E | 9/2016 | Chen et al. |
| 2002/0076409 A1 | 6/2002 | March et al. |
| 2006/0079528 A1 | 4/2006 | Finn et al. |
| 2006/0159713 A1 | 7/2006 | Brittain et al. |
| 2008/0146556 A1 | 6/2008 | Diebold et al. |
| 2010/0022512 A1 | 1/2010 | Wisdom et al. |
| 2010/0216858 A1 | 8/2010 | Popek et al. |

(Continued)

FOREIGN PATENT DOCUMENTS

| | | |
|---|---|---|
| CL | 0501-2003 | 3/2003 |
| CL | 2272-2005 | 9/2005 |

(Continued)

OTHER PUBLICATIONS

Bristol-Myers Squibb (BMS) "Study of Dasatinib and Bendamustine in Chronic Lymphocytic Leukemia" [online], Apr. 22, 2009 [retrieved on Aug. 6, 2017]. Retrieved from the Internet: ClinicalTrials.gov.*
Advanced Accelerator Applications, Ongoing Clinical Studies with Advanced Accelerator Applications Pipeline Candidates. Retrieved online at: http://www.adacap.com/research-development/clinical-trials/ (2014) (Year: 2014).*
Kampa-Schittenhelm et al., "Quizartinib (AC220) is a potent second generation class III tyrosine kinase inhibitor that displays a distinct inhibition profile against mutant-FLT3, -PDGFRA and -KIT isoforms," Molecular Cancer, 2013 12:19 1-15 [Abstract] (Year: 2013).*
Xiao-Rong et al., Database medline NLM24998648 May 2014 (Year: 2014).*

(Continued)

*Primary Examiner* — Amanda L Aguirre
(74) *Attorney, Agent, or Firm* — McCarter & English, LLP; Yu Lu; Wei Song

(57) ABSTRACT

The present invention is directed to a combination comprising a class III receptor tyrosine kinase inhibitor and a compound of formula I or a pharmaceutically acceptable salt thereof:

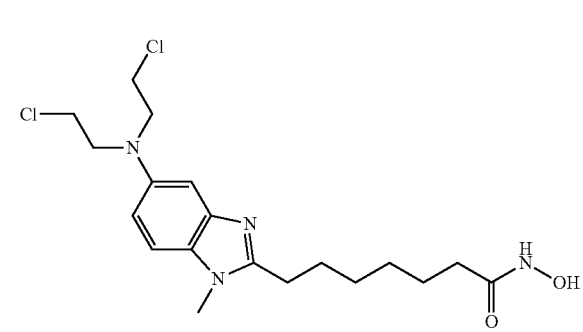

to a pharmaceutical composition and to a kit both comprising said combination, to the combination, composition or kit for use in the treatment of cancer, and to a method of treatment of cancer in a patient in need thereof comprising administering to said patient an effective amount of said combination, composition or kit.

22 Claims, 4 Drawing Sheets

(56) References Cited

U.S. PATENT DOCUMENTS

| | | |
|---|---|---|
| 2011/0190363 A1 | 8/2011 | Drager et al. |
| 2011/0311624 A1 | 12/2011 | Loury et al. |
| 2013/0209558 A1 | 8/2013 | Patzak et al. |
| 2015/0086551 A1 | 3/2015 | Chen et al. |
| 2017/0095482 A1 | 4/2017 | Mehrling |
| 2017/0151218 A1 | 6/2017 | Mehrling et al. |
| 2017/0189382 A1 | 7/2017 | Mehrling et al. |
| 2017/0296513 A1 | 10/2017 | Mehrling et al. |

FOREIGN PATENT DOCUMENTS

| | | | |
|---|---|---|---|
| CL | 3232-2006 | 11/2006 | |
| CN | 1764648 A | 4/2006 | |
| CN | 101084876 A | 12/2007 | |
| CN | 101928234 A | 12/2010 | |
| CN | 102993102 A | 3/2013 | |
| DE | 34727 A1 | 12/1964 | |
| EP | 0717638 B1 | 3/2002 | |
| JP | 2007-531793 A | 11/2007 | |
| WO | 1995/030442 A1 | 11/1995 | |
| WO | 2002/010161 A1 | 2/2002 | |
| WO | 0222577 A2 | 3/2002 | |
| WO | 2002/026696 A1 | 4/2002 | |
| WO | 2004/076386 A2 | 9/2004 | |
| WO | 2005/097747 A1 | 10/2005 | |
| WO | 2006/120456 A1 | 11/2006 | |
| WO | 2007/134169 A2 | 11/2007 | |
| WO | 2008/050125 A1 | 5/2008 | |
| WO | 2008/067027 A2 | 6/2008 | |
| WO | 2009/036016 A1 | 3/2009 | |
| WO | 2009/067453 A1 | 5/2009 | |
| WO | 2009/100045 A1 | 8/2009 | |
| WO | 2010/042568 A1 | 4/2010 | |
| WO | 2010/075542 A1 | 7/2010 | |
| WO | 2010/085377 A2 | 7/2010 | |
| WO | 2010/097700 A1 | 9/2010 | |
| WO | 2013/039488 A1 | 3/2013 | |
| WO | 2013/040286 A2 | 3/2013 | |
| WO | WO 2013040286 A2 * | 3/2013 | ............ A61K 31/16 |
| WO | 2013/113838 A1 | 8/2013 | |
| WO | 2015/085289 A1 | 6/2015 | |
| WO | 2015/181154 A1 | 12/2015 | |
| WO | 2015/181157 A1 | 12/2015 | |
| WO | 2016/087950 A1 | 6/2016 | |

OTHER PUBLICATIONS

Anastasia, et al., "Bendamustine for Hodgkin Lymphoma Patients Failing Autologous or Autologous and Allogeneic Stem Cell Transpantation: A Retrospective Study of the Fondazione Italiana Linfomi", British Journal of Haematology, 166:140-153 (2014).
Bachmann et al., "Epigenetic silencing of BIM in glucocorticoid poor-responsive pediatric acute lymphoblastic leukemia, and its reversal by histone deacetylase inhibition," Blood, 116(16):3013-3022 (2010).
Barendsen et al, "Inhibition of TPA-Induced Monocytic Differentiation in THP01 Human Monocytic Leukemic Cells by Staurosporine, a Potent Protein Kinase C Inhibitor", Leukemia Research 14(5):467-474, 1990.
Barman Balfour, J.A., et al., "Bendamustine", Drugs, 61(5):631-638 (2001).
Botrugno, et al., "Molecular Pathways: Old Drugs Define New Pathways: Non-Histone Acetylation at the Crossroads of the DNA Damage Response and Autophagy", Clin Cancer Res. 18(9):2436-42, 2012.
Braga et al., "Crystal Polymorphism and Multiple Crystal Forms", Struct Bond. 2009, 132:25-50, 2009.
Brewster, M.E., et al., "Cyclodextrins as Pharmaceutical Solubilizers," Adv. Drug Delivery Rev., 59:645-666 (2007).
Bueno, et al., "Preliminary Experience of the Spanish Compassionate Use Registry of Bendamustine in Patients with Relapsed and/or Refractory Multiple Myeloma", Blood 120(21), 2012, 4035.
Buglio D. et al., "Vorinostat inhibits STAT6-mediated TH2 cytokine and TARC production and induces cell death in Hodgkin lymphoma cell lines", Blood, 112 (4):1424-1433, Aug. 15, 2008.
Cai, et al., "Discovery of 7-(4-(3-Ethynylphenylamino)-7-ethoxyquinazolin-6-yloxy)-N-hydroxyheptanamide (CUDC-101) as Potent Multi-Acting HDAC, EGFR, and HER2 Inhibitor for Treatment of Cancer," J. Med. Chem., 53:2000-2009 (2010).
Cai, et al., "Solubilization of vorinostat by cyclodextrins," J. Clin. Pharm. Thera., 35:521-526 (2010).
Cancer [online], [retrieved on Jun. 7, 2007] Retrieved from the Internet, URL: http://www.nlm.nih.gov/medlineplus/cancer.html.
Chamberlain, et al., "Salvage Therapy with Bendamustine for Methotrexate Refractory Recurrent Primary CNS Lympohma: A Restrospective Case Series", J Neurooncology 118:155-162, 2014.
Chen, et al., "Dexamethasone and Vorinostat Cooperatively Promote Differentiation and Apoptosis in Kasumi-1 Leukemia Cells Through Ubiquitination and Degradation of AML1-ETO", Database Medline [online] —US National Library of Medicine (NLM), Bethesda, MD, US, XP002742548, Database Accession No. NLM24103869 [Abstract] (Sep. 2013).
Chow et al., "In Vitro Induction of Apoptosis of Neoplastic Cells in Low-Grade Non-Hodgkin's Lymphomas Using Combinations of Established Cytotoxic Drugs with Bendamustine", Haematologica, 86:485-493 (2001).
ClinicalTrials.gov, "A Phase 1 Study to Investigate the Safety, Pharmacokinetic Profiles and the Efficacy of EDO-S101, a First-in-Class Alkylating Histone Deacetylase Inhibition (HDACi) Fusion Molecule, in Relapsed/Refractory Hematologic Malignancies," Clinical Trials Identifier: NCT02576496 (Oct. 14, 2015)[Downloaded from: https://clinicaltrials.gov/archive/NCT02576496/2015_10_14].
Corazzelli, et al., "Efficacy and Safety of Bendamustine for the Treatment of Patients with Recurring Hodgkin Lymphoma", British Journal of Haematology, 2013; 160:207-215.
De Filippi et al., "The First-in-Class Alkylating Histone-Deacetylase Inhibitor(HDACi) Fusion Molecule EDO-S101 Exerts Potent Preclinical Activity Against Tumor Cells of Hodgkin Lymphoma (HL) Including Bendamustine-Resistant Clones" ASH, 57th annual meeting and exposition, Dec. 2015, Abstract 2481.
De Filippi, R., et al., "The First-in-Class Alkylating Histone-Deacetylase Inhibitor (HDACi) Fusion Molecule Edo-S101 Exerts Potent Preclinical Activity Against Tumor Cells of Hodgkin Lymphoma (HL) Including Bendamustine-Resistant clones"; Dec. 5-8, 2015 [Downloaded from: [ttps://ash.confex.com/ash/2015/webprogram/Paper84797.html].
DeAngelo, et al, "Phase 1 Clinical Results with Tandutinib (MLN518), a Novel FLT3 Antagonist, in Patients with Acute Myelogenous Leukemia or High-Risk Myelodysplastic Syndrome: Safety, Pharmacokinetics, and Pharmacodynamics", Blood 108(12):3674-3681, 2006.
Furumai, et al., "Potent Histone Deacetylase Inhibitors Built from Trichostatin A and Cyclic Tetrapeptide Antibiotics Including Trapoxin," PNAS, 98(1):87-92 (2001).
Ghesquières et al., "Clinical experience of bendamustine in relapsed refractory Hodgkin lymphoma: a retrospective analysis of the French Hodgkin lymphoma: a retrospective analysis of the French compassionate use of program in 28 patients", Leukemia & Lymphoma, 54(11):2399-2404 (2013).
Golub et al., "Molecular Classification of Cancer: Class Discovery and Class Prediction by Gene Expression Monitoring," Science, 286:531-537 (1999).
Griffith et al., "Novel Platinum Pyridinehydroxamic Acid Complexes: Synthesis, Characterisation, X-ray crystallographic Study of Nitric Oxide Related Properties," Polyhedron, 26:4697-4706 (2007).
Griffith, et al., "A Novel Anti-Cancer Bifunctional Platinum Drug Candidate with Dual DNA Binding and Histone Deacetylase Inhibitory Activity," Chem. Commun., 44:6735-6737 (2009).
Harrison, S J et al., "High Response Rates with the Combination of Bortezomib. Dexamethasone and the Pan-HistoneDeacetylase Inhibitor Romidepsin in Patients with Relapsed or Refractory Multiple Myeloma in a Phase 1/11 clinical Trial". Blood (ASH Annual Meeting Abstracts), 112:Abstract 3698, 2008.

(56) References Cited

OTHER PUBLICATIONS

Hedgethorne, K., et al, "FORETINIB, c-Met and VEGFR-2 Inhibitor Oncolytic", Drugs of the Future, 35(11) 2010 pp. 893-902.
Herold et al., "BOP Versus COP in Advanced Low-Grade Non-Hodkin's Lymphomas—Results of a Randomized Multicenter Study", Blood, 94(Suppl 1):262a (1999) (Abstract #4382).
Herold, et al., "Bendamustine, Vincristine and Prednisone (BOP) Versus Cyclophosphamide, Vincristine and Prednisone (COP) in Advanced Indolent Non-Hodkin's Lympoma and Mantle Cell Lymphoma: Results of a Radmonised Phase III Trial (OSHO# 19)", J Cancer Res Clin Oncol 2006, 132:105-112.
Hoffman et al., "Brentuximab Vedotin Plus Bendamustine Active in Heavily Pretreated Hodgkin Lymphoma, ALCL" Cancer Therapy Advisor Dec. 7, 2015, Orlando FL <http://www.cancertherapyadvisor.com/ash-2015/hodgkin-lymphoma-alcl-brentuximab-vedotin-better-treatment-risk/article/458249/>.
J. Han van Krieken, "New developments in the pathology of malignant lymphoma Areview of the literature published from Jan.-Apr. 2016" J Hematopathol (2016) 9:73-83.
Kaufman, Jonathan L., et al., "Lenalidomide. Bortezomib. and Dexamethasone (RVD) in Combination with Vorinostat As Front-Line Therapy for Patients with Multiple Myeloma (MM): Results of a Phase 1 Study", Blood, 120.(21):336, Nov. 16, 2012.
Keating, et al., "Bendamustine," Nature Rev./Drug Disc., 7:473-474 (2008).
Knauf, "Bendamustine in the treatment of chronic lymphocytic leukemia," Exp. Rev. Anticancer Ther., 9(2):165-174 (2009).
Kollmannsberger et al., "Phase II study of bendamustine in patients with relapsed or cisplatin-refractory germ cell cancer," Anti-Cancer Drugs, 11:535-539 (2000).
Lala et al., Role of nitric oxide in tumor progression: Lessons from experimental tumors, Cancer and Metastasis Reviews (1998), 17,91-106.
Layman et al, "Severe and prolonged lymphopenia observed in patients treated with bendamustine and erlotinib for metastatic triple negative breast cancer", Cancer Chemotherapy and Pharma 2013 (71) pp. 1183-1190.
Lentzsch, et al., "Combination of Bendamustine, Lenalidomide, and Dexamethasoen (BLD) in Patients with Relapsed or Refractory Multiple Myeloma is Feasible and Highly Effective: Results of Phase 1/2 Open-Lable, Dose Esclation Study", Blood 119(20):4608-4613, 2012.
Leoni, "Bendamustine: Rescue of an Effective Antineoplastic Agent From the Mid-Twentieth Century", Semin Hematol., 48 Suppl 1:S4-11 (2011).
Leoni, et al., "Bendamustine (Treanda Displays a Distinct Pattern of Cytotoxicity and Unique Mechanistic Features Comparred with Other Alkylating Agents", Clin Cancer Res. 2008;14:309-17. 8 8.
Liu et al., "A DNA/HDAC dual-targeting drug CY190602 with significantly enhanced anticancer potency," EMBO Mol. Med., 12 pages, Published online: Mar. 9, 2015.
Liu, "Characterization of TCL1-Tg:P53-/-Mice that Resemble Human Chronic Lymphocytic Leukemia with 17P-Deletion," UT GSBS Thesis, Graduate School of Biomedical Sciences, Digital Commons@The Texas Medical Center, May, 2013.
Loftsson, et al., "Cyclodextrins and their pharmaceutical applications," Intl. J. Pharmaceutics, 329:1-11 (2007).
Lopez-Iglesias et al., I "Preclinical anti-myeloma activity of the alkylating-HDACi molecule EDO-S101 through DNA-damaging and HDACi effects" Poster Jun. 1, 2014 (<http://mundipharma-edo.com/2014/06/01/preclinical-anti-myeloma-activity-of-the-alkylating-hdaci-molecule-edo-s101-through-dna-damaging-and-hdaci-effects/>.
Ludwig, et al., "Bendamustine-Bortezomib-Dexamethasone is an Active and Well-Tolerated Regimen in Patients with Relapsed or Refractory Multiple Myeloma", Blood 123(7):985-991, 2014.
Marks, "Discovery and development of SAHA as an anticancer agent," Oncogene, 26:1351-1356 (2007).

Marmion, et al., "Hydroxamic Acids—An Intriguing Family of Enzyme Inhibitors and Biomedical Ligands," Eur. J. Inorg. Chem., 2004(15):3003-3016 (2004).
Meanwell, "Synopsis of Some Recent Tactical Application of Bioisoteres in Drug Design", J. Med. Chem, 2011, 54:2529-2591.
Mehrling, "Chemotherapy is getting 'smarter'", Future Oncol. (2015) 11(4), 549-552.
U.S. Appl. No. 13/143,155, filed Jul. 1, 2011, now U.S. Pat. No. 8,609,864, Granted.
U.S. Appl. No. 14/075,145, filed Nov. 8, 2013, now U.S. Pat. No. 9,096,627, Granted.
U.S. Appl. No. 14/972,750, filed Dec. 17, 2015, now Re. 46,144, Granted.
U.S. Appl. No. 14/345,562, filed Nov. 3, 2014, now U.S. Pat. No. 8,962,855, Granted.
U.S. Appl. No. 14/347,397, filed Mar. 26, 2014, now U.S. Pat. No. 8,962,855, Granted.
U.S. Appl. No. 14/374,995, filed Nov. 28, 2016, 2015-0086551-A1, Pending.
U.S. Appl. No. 15/290,546, filed Oct. 11, 2016, Not Yet Published, Pending.
U.S. Appl. No. 15/314,162, filed Nov. 28, 2016, 2017-0151218 A1, Pending.
U.S. Appl. No. 15/314,172, filed Nov. 28, 2016, Not Yet Published, Pending.
U.S. Appl. No. 15/314,180, filed Nov. 28, 2016, Not Yet Published, Pending.
Valdez et al., Synergistic cytotoxicity of the DNA alkylating agent busulfan, nucleoside analogs and suberoylanilide hydroxamic acid in lymphoma cell lines. Leuk Lymphoma. May 2012;53(5):973-81.
Viel et al., Optimizing glioblastoma temozolomide chemotherapy employing lentiviral-based anti-MGMT shRNA technology. Mol Ther. Mar. 2013;21(3):570-9.
Vlachostergios et al., Bortezomib overcomes MGMT-related resistance of glioblastoma cell lines to temozolomide in a schedule-dependent manner. Invest New Drugs. Oct. 2013;31(5):1169-81.
Von Tresckow et al., An update on emerging drugs for Hodgkin lymphoma. Expert Opin Emerg Drugs. Jun. 2014;19(2):215-24.
Wang et al., Independent validation of a model using cell line chemosensitivity to predict response to therapy. J Natl Cancer Inst. Sep. 4, 2013;105(17):1284-91.
Weil et al., Breast cancer metastasis to the central nervous system. Am J Pathol. Oct. 2005;167(4):913-20.
Wilson et al., Histone deacetylase 3 (HDAC3) and other class I HDACs regulate colon cell maturation and p21 expression and are deregulated in human colon cancer. J Biol Chem. May 12, 2006;281(19):13548-58.
Witzel et al., Long-term tumor remission under trastuzumab treatment for HER2 positive metastatic breast cancer—results from the HER-OS patient registry. BMC Cancer. Nov. 4, 2014;14:806. 7 pages.
Xiao et al., Antineutrophil cytoplasmic autoantibodies specific for myeloperoxidase cause glomerulonephritis and vasculitis in mice. J Clin Invest. Oct. 2002;110(7):955-63.
Yardley, Drug resistance and the role of combination chemotherapy in improving patient outcomes. Int J Breast Cancer. 2013;2013:137414. 15 pages.
Zhu et al., Histone deacetylase 3 implicated in the pathogenesis of children glioma by promoting glioma cell proliferation and migration. Brain Res. Jul. 3, 2013;1520:15-22.
Zinzani et al., Brentuximab Vedotin in Transplant-Naïve Relapsed/Refractory Hodgkin Lymphoma: Experience in 30 Patients Oncologist. Dec. 2015;20(12):1413-6.
Al-Ani et al., Changes in urinary metabolomic profile during relapsing renal vasculitis. Sci Rep. Dec. 1, 2016;6:38074. 11 pages.
Alfarouk et al., Resistance to cancer chemotherapy: failure in drug response from ADME to P-gp. Cancer Cell Int. Jul. 15, 2015;15:71.
American Cancer Society, How does chemotherapy affect the risk of second cancers? Retrieved online at: https://www.cancer.org/treatment/treatments-and-side-effects/physical-side-effects/second-cancers-in-adults/chemotherapy.html. 5 pages (2017).

(56) References Cited

OTHER PUBLICATIONS

Andersson et al., Discovery of novel drug sensitivities in T-PLL by high-throughput ex vivo drug testing and mutation profiling. Leukemia. Aug. 14, 2017. pp. 1-14.

Attal et al., Lenalidomide, Bortezomib, and Dexamethasone with Transplantation for Myeloma. The New England Journal of Medicine. Apr. 6, 2017;376:1311-1320.

Bernhard et al., Quality of life and quality-adjusted survival (Q-TWiST) in patients receiving dose-intensive or standard dose chemotherapy for high-risk primary breast cancer. Br J Cancer. Jan. 15, 2008;98(1):25-33.

Besse et al., The first in class, alkylator-histone-deacetylase-inhibitor fusion molecule EDO-S101 in combination with proteasome inhibitors induces highly synergistic pro-apoptotic signaling through UPR activiation and suppression of c-Myc and BCL2 in multiple meyloma. ASH, 2016.

Besse et al., The first-in-class alkylating HDAC inhibitor EDO-S101 is highly synergistic with proteasome inhibition against multiple myeloma through activation of multiple pathways. Blood Cancer J. Jul. 2017;7(7):e589. 4 pages.

Besse et al., The First-in-Class, Alkylator-Histone-Deacetylase-Inhibitor Fusion Molecule EDO-S101 in Combination with Proteasome Inhibitors Induces Highly Synergistic Pro-Apoptotic Signaling through UPR Activation and Suppression of c-Myc and BCL2 in Multiple Myeloma. 58th ASH Annual Meeting, San Diego, Dec. 3-6, 2016, Publication No. 4466. 1 page.

Bose et al., Histone deacetylase inhibitor (HDACI) mechanisms of action: emerging insights. Pharmacol Ther. Sep. 2014;143(3):323-36.

Bruce et al., Glioblastoma Multiforme Treatment & Management. Medscape. Retrieved online at: https://emedicine.medscape.com/article/283252-treatment. 20 pages. Jun. 14, 2017.

Cai et al., Combination of bendamustine and entinostat synergistically inhibits proliferation of multiple myeloma cells via ainduction of apoptosis and DNA damage response. Cancer Lett. Jul. 28, 2013;335(2):343-50.

Campos et al., Expression of nuclear receptor corepressors and class I histone deacetylases in astrocytic gliomas. Cancer Sci. Feb. 2011;102(2):387-92.

Chen et al., A 71-gene signature of Trail sensitivity in cancer cells. Mol Cancer Ther. Jan. 2012;11(1):34-44.

Chen et al., Discovery of a Novel, Efficient, and Scalable Route to Bendamustine Hydrochloride: The API in Treanda. Org Process Res Dev. 2011;15(5):1063-1072.

Chesi et al., Drug response in a genetically engineered mouse model of multiple myeloma is predictive of clinical efficacy. Blood. Jul. 12, 2012;120(2):376-85.

Chesi et al., Identification of Novel Therapeutic Targets in the Clinically Predictive Vk*MYC Mouse Model of Multple Myeloma. ASH, 2 pages. 2014.

Chesi et al., Identification of Novel Therapeutic Targets in the Clinically Predictive Vk*MYC Mouse Model of Multple Myeloma. Blood. 2014;124:415.

Chisholm et al., Emergence of drug tolerance in cancer cell populations: an evolutionary outcome of selection, nongenetic instability, and stress-induced adaptation. Cancer Res Mar. 15, 2015;75(6):930-9.

Ciavatta et al., Epigenetic basis for aberrant upregulation of autoantigen genes in humans with ANCA vasculitis. J Clin nvest. Sep. 2010;120(9):3209-19.

ClinicalTrials.gov, Bendamustine, Lenalidomide (Revlimid®) and Dexamethasone (BRd) as 2nd-line Therapy for Patients With Relapsed or Refractory Multiple Myeloma (BRd). Clinical Trials Identifier: NCT01701076, Aug. 24, 2016.

Connors, Hodgkin lymphoma: special challenges and solutions. Hematol Oncol. Jun. 2015;33 Suppl 1:21-4.

Cooke et al., Spontaneous onset and transplant models of the Vk*MYC mouse show immunological sequelae comparable to human multiple myeloma. J Transl Med. Sep. 6, 2016;14:259. 12 pages.

Curigliano et al., Cardiovascular toxicity induced by chemotherapy, targeted agents and radiotherapy: ESMO Clinical Practice Guidelines. Annals of Oncology. Oct. 2012;23(Suppl. 7):vii155-vii166.

De Filippi et al., Continuous Exposure to Bendamustine (BDM) Results in Stable Upregulation of CD30 and Increased Sensitivity to Brentuximab Vedotin (BV) in Tumor Cells of Hodgkin Lymphoma HL. Istituto Nazionale Tumor, IRCCS-Fondazione Pascale, Dec. 6, 2015. 1k page.

DeSouza et al., Has the survival of patients with glioblastoma changed over the years? Br J Cancer. Jan. 19, 2016;114(2):146-50.

Drogaris et al., Histone deacetylase inhibitors globally enhance h3/h4 tail acetylation without affecting h3 lysine 56 acetylation. Sci Rep. 2012;2:220. 12 pages.

Döhner et al., Diagnosis and management of acute myeloid leukemia in adults: recommendations from an international expert panel, on behalf of the European LeukemiaNet. Blood. Jan. 21, 2010;115(3):453-74.

EU Clinical Trials Register, EudraCT No. 2005-002051-41. 13 pages. Dec. 7, 2016.

EU Clinical Trials Register, EudraCT No. 2005-006083-5T 28 pages. Jun. 1, 2016.

Eurordis, Rare Diseases Europe, Why Research on Rare Diseases? Position Paper. Retrieved online at: www.eurordis.org. 14 pages. Oct. 2010.

Fei et al., Development of clinically relevant orthotopic xenograft mouse model of metastatic lung cancer and glioblastoma through surgical tumor tissues injection with trocar. J Exp Clin Cancer Res. Jun. 29, 2010;29:84.

Festuccia et al., Enhancement of radiosensitivity by the novel anticancer quinolone derivative vosaroxin in preclinical glioblastoma models. EJC, European Journal of Cancer. Dec. 2016;69(Suppl 1):562. Abstract 174, Poster P145.

Festuccia et al., Targeting glioblastoma with UniPR1331, a new and stable bioavailable small molecule inhibiting Ephephrin interaction: In vitro and in vivo evidence. EJC, European Journal of Cancer. Dec. 2016;69(Suppl 1), Abstract 71, Poster P042.

Frew et al., Enhancing the apoptotic and therapeutic effects of HDAC inhibitors. Cancer Lett. Aug. 8, 2009;280(2):125-33.

Graham RL, Cooper B, Krause JR. T-cell prolymphocytic leukemia. Proc (Bayl Univ Med Cent). Jan. 2013;26(1):19-21.

Greaves et al., Clonal evolution in cancer. Nature. Jan. 18, 2012;481(7381):306-13.

Groselj et al., Histone deacetylase inhibitors as radiosensitisers: effects on DNA damage signalling and repair. Br J Cancer. Mar. 5, 2013;108(4):748-54.

Hancock et al., HDAC inhibitor therapy in autoimmunity and transplantation. Ann Rheum Dis. Apr. 2012;71 Suppl 2: 46-54.

Hegi et al., MGMT gene silencing and benefit from temozolomide in glioblastoma. N Engl J Med. Mar. 10, 2005;352(10):997-1003.

Her et al., Targeting DNA Double-strand Break Repair in Cancer Therapy. Journal of Molecular and Genetic Medicine. Dec. 31, 2015;9:e106, 1 page.

Howlader et al., Contributions of Subtypes of Non-Hodgkin Lymphoma to Mortality Trends. Cancer Epidemiol Biomarkers Prev. Jan. 2016;25(1):174-9.

Jagannath et al., Bortezomib in combination with dexamethasone for the treatment of patients with relapsed and/or refractory multiple myeloma with less than optimal response to bortezomib alone. Haematologica. Jul. 2006;91(7):929-34.

Jawhari et al., In Vitro and In Vivo Preclinical Activity of EDO-S101 in Hodgkin Lymphoma. Haematologica. 2016;101(s5):6-7, Abstract P037.

Jennette et al., Pathogenesis of antineutrophil cytoplasmic autoantibody-mediated disease. Nat Rev Rheumatol. Aug. 2014;10(8):463-73.

Jiang et al., A mammalian functional-genetic approach to characterizing cancer therapeutics. Nature Chemical Biology. Feb. 2011;7:92-100.

Kaddour et al., Transmission of Induced Chromosomal Aberrations through Successive Mitotic Divisions in Human Lymphocytes after In Vitro and ?In? Vivo Radiation. Scientific Reports. Jun. 12, 2017;7:3291, 11 pages.

(56) References Cited

OTHER PUBLICATIONS

Kallenberg, Pathogenesis of ANCA-associated vasculitides. Ann Rheum Dis. Mar. 2011;70 Suppl 1:i59-63.

Kalsi et al., The impact of low-grade toxicity in older people with cancer undergoing chemotherapy. Br J Cancer. Dec. 9, 2014;111(12)-2224-8.

Khot et al., Panobinostat in lymphoid and myeloid malignancies. Expert Opin Investig Drugs. Sep. 2013;22(9):1211-23.

Kigawa J. New strategy for overcoming resistance to chemotherapy of ovarian cancer. Yonago Acta Med. Jun. 2013;56(2):43-50.

Kim et al., Histone deacetylase inhibitors: molecular mechanisms of action and clinical trials as anti-cancer drugs. Am J Transl Res. Feb. 2011;3(2):166-79.

Knittel et al., Two mouse models reveal an actionable PARP1 dependence in aggressive chronic lymphocytic leukemia. Nat Commun. Jul. 28, 2017;8(1):153. 13 pages.

Kraus et al., EDO-S101, A New Alkylating Histone-Deacetylase Inhibitor (HDAC) Fusion Molecule has Superior Activity Against Myeloma and B Cell Lympoma and Strong Synergy, With Proteasome Inhibitors in vitro. ASH, 2014.

Kraus et al., EDO-S101, A New Alkylating Histone-Deacetylase Inhibitor (HDACi) Fusion Molecule, has Superior Activity Against Myeloma and B Cell Lympoma and Strong Synergy With Proteasome Inhibitors in vitro. ASH, 2014. Publication No. 2249.

Kraus et al., EDO-S101, A New Alkylating Histone-Deacetylase Inhibitor (HDACi) Fusion Molecule, Has Superior Activity Against Myeloma and B Cell Lympoma and Strong Synergy with Proteasome Inhibitors in vitro. Blood. 2014;124;2249.

Le Moigne et al., The p97 Inhibitor CB-5083 Is a Unique Disrupter of Protein Homeostasis in Models of Multiple Myeloma. Molecular Cancer Therapeutics. Nov. 2017;16(11):2375-2386.

Leung-Hagesteijn et al., Xbp1s-negative tumor B cells and preplasmablasts mediate therapeutic proteasome inhibitor resistance in multiple myeloma. Cancer Cell. Sep. 9, 2013;24(3):289-304.

Liby et al., Elevated and Deregulated Expression of HDAC3 in Human Astrocytic Glial Tumours. Folia Biologica (Praha). 2006;52:21-33.

Lin et al., Anti-rheumatic activities of histone deacetylase (HDAC) inhibitors in vivo in collagen-induced arthritis in rodents. Br J Pharmacal. Apr. 2007;150(7):862-72.

Lin et al., Treatment of Brain Metastases. J Clin Oncol. Oct. 20, 2015;33(30):3475-84.

Little et al., Experimental autoimmune vasculitis: an animal model of anti-neutrophil cytoplasmic autoantibody-associated systemic vasculitis. Am J Pathol. Apr. 2009;174(4):1212-20.

Little et al., Therapeutic effect of anti-TNF-alpha antibodies in an experimental model of anti-neutrophil cytoplasm antibody-associated systemic vasculitis. J Am Sac Nephrol. Jan. 2006;17(1):160-9.

Lombardi et al., Predictors of survival and effect of short (40 Gy) or standard-course (60 Gy) irradiation plus concomitant temozolomide in elderly patients with glioblastoma: a multicenter retrospective study of AINO (Italian Association of Neuro-Oncology). J Neurooncol. Nov. 2015;125(2):359-67.

Lopez-Iglesias et al., Preclinical anti-myeloma activity of EDO-S101, a new bendamustine-derived molecule with added HDACi activity, through potent DNA damage induction and impairment of DNA repair. J Hematol Oncol. Jun. 20, 2017;10(1):127. 14 pages.

Lopez-Iglesias et al., Preclinical Anti-Myeloma Activity of the Alkylating-HDACi Molecule EDO-S101 Through DNA-Damaging and HDACi Effects. EHA 2014 Poster, Jun. 12, 2014.

Lopez-Iglesias et al., Preclinical antimyeloma activity of EDO-S101 (bendamustine-vorinostat fusion molecule) through DNA-damaging and HDACi effects. 15th International Myeloma Workshop. Sep. 23-26, 2015. Rome, Italy. Clinical Lymphoma, Myeloma & Leukemia. Sep. 2015;15(3 Suppl. 3):e218, Abstract P0-238.

Lopez-Iglesias et al., The Alkylating Histone Deacetylase Inhibitor Fusion Molecule EDO-S101 Displays Full Bi-Functional Properties in Preclinical Models of Hematological Malignancies. Blood. 2014;124:2100.

Lopez-Iglesias et al., The Hybrid Molecule, Edo-S101, Impairs Double Strand Breaks Repair in Multiple Myeloma and Synergizes with Bortezomib and Dexamethasone. Blood. 2015;126(23):5354-5354.

Lucio-Eterovic et al., Differential expression of 12 histone deacetylase (HDAC) genes in astrocytomas and normal brain tissue: class II and IV are hypoexpressed in glioblastomas. BMC Cancer. Aug. 19, 2008;8:243.

Marchion et al., Development of histone deacetylase inhibitors for cancer treatment. Expert Rev Anticancer Ther. Apr. 2007;7(4):583-98.

McInnis et al., Dysregulation of autoantigen genes in ANCA-associated vasculitis involves alternative transcripts and new protein synthesis. J Am Soc Nephrol. Feb. 2015;26(2):390-9.

Mehrling et al., Activity of the alkylating histone-deacetylase inhibition fusion molecule EDO-S-101 in preclinical models of human glioblastoma independent from MGMT expression. Journal of Clinical Oncology. May 29, 2017;33(Suppl. 15), Abstract e13031.

Mehrling et al., Is there hope to treat glioblastoma effectively? CNS Oncol. 2015;4(6):377-9.

Mehrling, Fusion Therapy, a New Approach to Combining Treatments. Drug Discovery World. 2016;71-76.

Mey et al., Bendamustine, lenalidomide and dexamethasone (BRd) has high activity as 2(nd)-line therapy for relapsed and refractory multiple myeloma—a phase II trial. Br J Haematol. Mar. 2017:176(5):770-782.

MRF, Melanoma Research Foundation, Melanoma Central Nervous System Metastases, Current Approaches, Challenges and Opportunities. 5 pages (2015).

O'Donnell et al., Cancer pharmacoethnicity: ethnic differences in susceptibility to the effects of chemotherapy. Clin Cancer Res. Aug. 1, 2009;15(15):4806-14.

O'Reilly et al., Urinary Soluble CD163 in Active Renal Vasculitis. J Am Soc Nephrol. Sep. 2016;27(9):2906-16.

Oken et al., Toxicity and response criteria of the Eastern Cooperative Oncology Group. Am J Clin Oncol. Dec. 1982;5(6):649-55.

Oriol et al., Outcome after relapse of acute lymphoblastic leukemia in adult patients included in four consecutive risk-adapted trials by the PETHEMA Study Group. Haematologica. Apr. 2010;95(4):589-596.

Phan et al., An update on ethnic differences in drug metabolism and toxicity from anti-cancer drugs. Expert Opin Drug Metab Toxicol. Nov. 2011;7(11):1395-410.

Puetzer et al., Towards novel strategies of targeting specific vulnerabilities of T-PLL cells. AACR Annual Meeting. Jul. 2017;77(Suppl 13), Abstract 1372.

Rasschaert et al., A phase I study of bendamustine hydrochloride administered day 1+2 every 3 weeks in patients with solid tumours. Br J Cancer. Jun. 4, 2007;96(11):1692-8.

Rasschaert et al., A phase I study of bendamustine hydrochloride administered once every 3 weeks in patients with solid tumors. Anticancer Drugs. Jun. 2007;18(5):587-95.

Rengstl et al., Small and big Hodgkin-Reed-Stemberg cells of Hodgkin lymphoma cell lines L-428 and L-1236 lack consistent differences in gene expression profiles and are capable to reconstitute each other. PLoS One. May 15, 2017;12(5):e0177378.

Rodriguez-Tenreiro y Sanchez, Hydrogels of Cyclodextrin Co-crosslinked and Interpenetrated for Controlled Drug Release. University of Santiago de Compostela, School of Pharmacy. pp. 29-32, (2006).

Santacruz et al., The prognostic impact of minimal residual disease in patients with chronic lymphocytic leukemia requiring first-line therapy. Haematologica. May 2014;99(5):873-80.

Sarkaria et al., Mechanisms of chemoresistance to alkylating agents in malignant glioma. Clin Cancer Res. May 15, 2008;14(10):2900-8.

Schöffski et al., Repeated administration of short infusions of bendamustine: a phase I study in patients with advanced progressive solid tumours. J Cancer Res Clin Oncol. Jan. 2000;126(1):41-7.

Schöffski et al., Weekly administration of bendamustine: a phase I study in patients with advanced progressive solid tumours. Ann Oncol. Jun. 2000;11(6):729-34.

(56) References Cited

OTHER PUBLICATIONS

Shah et al., Comprehensive analysis of MGMT promoter methylation: correlation with MGMT expression and clinical response in GBM. PLoS One. Jan. 7, 2011;6(1):e16146.
Simon, Optimal two-stage designs for phase II clinical trials. Control Clin Trials. Mar. 1989;10(1):1-10.
Song et al., Increased expression of histone deacetylase 2 is found in human gastric cancer. APMIS. 2005;113:264-8.
Stiborová et al., The synergistic effects of DNA-targeted chemotherapeutics and histone deacetylase inhibitors as therapeutic strategies for cancer treatment. Curr Med Chem. 2012;19(25):4218-38.
Storer, Design and analysis of phase I clinical trials. Biometrics. Sep. 1989;45(3):925-37.
Tesar et al., Limitations of standard immunosuppressive treatment in ANCA-associated vasculitis and lupus nephritis. Nephron Clin Pract. 2014;128(3-4):205-15.
Thurn et al., Rational therapeutic combinations with histone deacetylase inhibitors for the treatment of cancer. Future Oncol. Feb. 2011;7(2):263-83.
Trivedi et al., Management of Chemotherapy-Induced Peripheral Neuropathy. American Journal of Hematology / Oncology. Jan. 2015;11(1):4-10.
Mehrling, "Mundipharma EDO GmbH Announces FDA Investigational New Drug Approval of its First Anti-Cancer Compound, EDO-S101, for the Treatment of Patients with Relapsed/Refractory Haematologic Malignancies and Solid Tumours (http://mundipharma-edo.com/2015/07/31/mundipharma-edo-gmbh-announces-fda-investigational-new-drug-approval-of-its-first-anti-cancer-comound-deo-s101-for-the-treatment-of-patients-with-relapsedrefractory-haematologic-malignancies-and-s/)," EDO-S101 FDA IND Press Release—Basel, Switzerland, Jul. 31, 2015.
Mehrling, Mundipharma EDO GmbH announces first-in-human clinical trial of its lead compound, EDO-S101 (http://mundipharma-edo.com/2016/07/20/mundipharma-edo-gmbh-announces-first-in-human-clinical-trial-of-lead-compound-edo-s101/)—First-in-human clinical trial of its lead compound, EDO-S101, Switzerland, May 31, 2016, p. 1-2.
Mehrling, "The Alkylating-HDAC Inhibition Fusion Principle Taking Chemotherapy to the next Level with the First in class Molecule EDO-S101" Anti-Cancer Agents in Medicinal Chemistry, 2016, (16) pp. 20-28.
Miller, et al., "Histone Deacetylase Inhibitors," J. Med. Chem., 46(24):5097-5116 (2003).
Minucci, et al., "Histone deacetylase inhibitors and the promise of epigenetic (and more) treatments for cancer," Nat. Rev. Cancer, 6:38-51 (2006).
Moosman, et al., "Weekly Treatment with a Combination of Bortezomib and Bendamustine in Relapsed or Refractory Indolent Non-Hodgkin Lymphoma", Leukemia & Lymphoma 51(1):149-152, 2010.
Moradei, et al., "Histone Deacetylase Inhibitors: Latest Developments, Trends and Prospects," Curr. Med. Chem.—Anti-Cancer Agents, 5:529-560 (2005).
Moreau, et al: "Phase 1b Dose Escalation Study of Oral Quisinostat, a Histone Deacetylase Inhibitor (HDACi), in Combination With Velcade (Bortezomib) and Dexamethasone for Patients With Relapsed Multiple Myeloma (MM)", Blood, 122(21):1932, Nov. 15, 2013 (Abstract).
Moskowitz A.J. et al., "Phase II study of bendamustine in relapsed and refractory Hodgkin lymphoma", J.Clin. Oncol. Feb. 1, 2013; 31(4):456-60.
Moskowitz, et al., Leukemia & Lymphoma, Nov. 2013; 54(11): 2339-2340.
Munker, et al., "Activity of Tyrosine Kinase Inhibitors in Multiple Myeloma", Blood 110(11) part 2, 274B, 2007, Abstract No. 4804.
Ocio, E.M., et al., "Triple Combinations of the HDAC Inhibitor Panobinostat (LBH589) Plus Dexamethasone with Either Lenalidomide or Bortezomib are Highly Effective in a Multiple Myeloma Mouse Model", Blood, 110:Abstract 1514, 2007.
Offidani, et al., Efficacy and tolerability of bendamustine, bortezomib and dexamethasone in patients with relapsed=refractory multiple myeloma: a phase II study, Blood Cancer Journal, 3, 2013, e162.
Paris, et al., "Histone Deacetylase Inhibitors: From Bench to Clinic," J. Med. Chem., 51(6):1505-1529 (2008).
Pitha, et al., "Parenteral hydroxypropyl cyclodextrins: intravenous and intracerebral administration of lipophiles," J. Pharm. Sci., 83(6):833-837 (1994).
Poenisch, et al., "Bendamustine/Prednisone Versus Melphalane/Prednisone in the Primary Treatment of Multiple Myeloma: An Updated Analysis of the 94BP01 Protocol," Blood, 96, Suppl 1:759a (2000) (Abstract #3284, Poster Board #-Session: 748-111).
Ponisch, et al., "Combined Bendamustine, Prednisone and Bortezomib (BPV) in Patients with Relapsed or Refractory Multiple Myeloma", J Cancer Res Clin Oncol (2013) 139:499-508.
Ponisch, et al., "Treatment of Bendamustine and Prednisone in Patients with Newly Diagnosed Multiple Myeloma Results in Superior Complete Response Rate, Prolonged Time to Treatment Failure and Improved Quality of Life Compared to Treatment with Melphalan and Prednisone—A Randomzied Phase III Study of the East German Study Gruop of Hematology and Oncology (OSHO)", J Cancer Res Clin Oncol (2006) 132:205-212.
Pulsoni et al. "Bendamustine for Hodgkin lymphoma patients failing autologous or autologous and allogeneic stem cell transplantation: a retrospective study of the Fondazione Italiana Linfomi", British Journal of Haematology, 2014, 166, 140-153.
Rajewski et al., "Preliminary safety evaluation of parenterally administered sulfoalkyl ether ?-cyclodextrin derivatives," J. Pharm. Sci., 84(8):927-932 (1995).
Rasheed, et al., "Histone Deacetylase Inhibitors in Cancer Therapy", Expert Opin. on Investig. Drugs,2007 16(5):659-678.
Sanchez et al., "Anti-Myeloma Effects of Carfilzomib with Cyclophosphamide (CY) or Bendamustine (Ben)," Blood, 120(21)[Abstract] (2012).
Saulnier et al., "An Efficient Method for the Synthesis of Guanidino Prodrugs," Bioorganic & Medicinal Chemistry Letters, 4(16):1985-1990 (1994).
Sawas A. et al., "The Combination of Brentuximab Vedotin (Bv) and Bendamustine (B) Demonstrates Marked Activity in Heavily Treated Patients with Relapsed or Refractory Hodgkin Lymphoma (HL) and Anaplastic Large T-Cell Lymphoma (ALCL): Results of an International Multi Center Phase I/II Experience". Oral Presentation at 57th American Society of Hematology (ASH9 Annual Meeting & Exposition; Dec. 5-8, 2015; Orlando, FL.<http://www.bloodjournal.org/content/126/23/586?sso-checked=true>.
Shipley, et al., "Acute Myelogenous Leukemia", Experimental Hematology, 2009, 37:649-650.
Sturn, et al., "Genesis: Cluster Analysis of Microarray Data", Bloinformatics, 2002;18:207-8.
Vippagunta et al. "Crystalline Solids," Advanced Drug Delivery Reviews, 2001, 48, pp. 3-26.
Vyas et al., "Cyclodextrin based novel drug delivery systems," J. Incl. Phenom. Macrocycl. Chem., 62:23-42 (2008).
Wang et al, "Effect of histone deacetylase inhibitor NL101 on rat neurons" XP002740556 Database Medline accession No. NLM24998648 ZheJiang Hua Xue Xue Bao, Yi xue ban 43 (3) May 2014, pp. 265-272 Abstract.
Wang et al., "Toward Selective Histone Deacetylase Inhibitor Design: Homology Modeling, Docking Studies, and Molecular Dynamics Simulations of Human Class 1 Histone Deacetylases", J. Med. Chem., 48:6936-6947 (2005).
Wang, et al., "Phase 1 Trial of Linifanib (ABT-869) in Patients with Refractory or Relapsed Acute Myeloid Leukemia", Leukemia & Lymphoma, 2012, 53(8):1543-1551.
Wilson, W.H., et al, "Relationship of p53, bcl-2, and Tumor Proliferation to Clinical Drug Resistance in Non-Hodgkin's Lymphomas", Blood, 89(2):601-609, Jan. 15, 1997.
Xie, et al. "Quantitative Structure-Activity Relationship Study of Histone Deacetylase Inhibitors," Curr. Med. Chem.—Anti-Cancer Agents, 4:273-299 (2004).
Yan et al., "Abstract 2741: Synergistic Inhibition of Tumor Growth and Overcoming Chemo-Resistance by Simultaneously Targeting

(56) References Cited

OTHER PUBLICATIONS

Key Components in DNA Damage/Repair, Epigenetic, and Putative Cancer Stem Cell Signaling Pathways Using Novel Dual-Functional DNA-Alkylating/HDAC Inhibitor and Tumor Suppressor Gene Nanoparticles in Cancer Research," Cancer Research, 72(8 Suppl):Abstract nr 2741, (2012).

Zulkowski, et al., "Regression of Brain Metastases from Breast Carcinoma after Chemotherapy with Bendamustine", J Cancer Res Clin Oncol, 2012, 128:111-113.

Krause et al., Tyrosine kinases as targets for cancer therapy. N Engl J Med. Jul. 14, 2005; 353(2):172-87.

Qian et al., Activity of PXD101, a histone deacetylase inhibitor, in preclinical ovarian cancer studies. Mol Cancer Ther. 2006; 5(8):2086-2095.

\* cited by examiner

PHARMACEUTICAL COMBINATION COMPRISING A CLASS III RECEPTOR TYROSINE KINASE INHIBITOR AND THE ALKYLATING HISTONE-DEACETYLASE INHIBITOR FUSION MOLECULE EDO-S101 TOGETHER WITH ITS USE IN THE TREATMENT OF CANCER

CROSS-REFERENCE TO RELATED APPLICATIONS

This application is a U.S. national stage filing under 35 U.S.C. § 371(c), of International Application No. PCT/EP2015/061569, filed on May 26, 2015, which claims foreign priority of U.K. Patent Application No. 1409488.2, filed on May 28, 2014. The entire contents of each of the aforementioned applications are incorporated herein by reference.

TECHNICAL FIELD

The present invention relates to combinations that are of use in the treatment of cancer such as hematologic cancer and breast cancer.

BACKGROUND TO THE INVENTION

Cancer is one of the most life threatening diseases. Cancer is a condition in which cells in a part of the body experience out-of-control growth. According to latest data from American Cancer Society, it is estimated there will be 1.67 million new cases of cancer in USA in 2014. Cancer is the second leading cause of death in the United States (second only to heart disease) and will claim more than 585,000 lives in 2014. In fact, it is estimated that 50% of all men and 33% of all women living in the United States will develop some type of cancer in their lifetime. Therefore cancer constitutes a major public health burden and represents a significant cost in the United States. These figures are reflected elsewhere across most countries globally, although the types of cancer and relative proportions of the population developing the cancers vary depending upon many different factors such including genetics and diet.

For decades surgery, chemotherapy, and radiation were the established treatments for various cancers. Patients usually receive a combination of these treatments depending upon the type and extent of their disease. But chemotherapy is the most important option for cancer patients when surgical treatment (i.e. the removal of diseased tissue) is impossible. While surgery is sometimes effective in removing tumors located at certain sites, for example, in the breast, colon, and skin, it cannot be used in the treatment of tumors located in other areas, such as the backbone, nor in the treatment of disseminated hematologic cancers include cancers of the blood and blood-forming tissues (such as the bone marrow). They include multiple myeloma, lymphoma and leukemia. Radiation therapy involves the exposure of living tissue to ionizing radiation causing death or damage to the exposed cells. Side effects from radiation therapy may be acute and temporary, while others may be irreversible. Chemotherapy involves the disruption of cell replication or cell metabolism. It is used most often in the treatment of breast, lung, and testicular cancer. One of the main causes of failure in this treatment of cancer is the development of drug resistance by the cancer cells, a serious problem that may lead to recurrence of disease or even death. Thus, more effective cancer treatments are needed.

Multiple myeloma is a significant and growing problem. It is a cancer arising from plasma cells. Normal plasma cells produce immunoglobulins to fight infection. In myeloma, the plasma cells become abnormal, multiply uncontrollably and release only one type of antibody—known as paraprotein—which has no useful function. It tends to accumulate in the bone marrow and circulate in the blood and can be detected in the urine as well. It affects multiple sites in the body (hence 'multiple' myeloma) where bone marrow is normally active in adults. The main forms of multiple myeloma (or myeloma as it is also referred to) are active myeloma, plasmacytoma, light chain myeloma and non-secretory myeloma. The number of new cases of myeloma in the US in 2011 was 6.1 per 100,000 men and women per year and the percentage survival rate beyond five years was 45%. It is estimated that the number of new cases in the US in 2014 will be over 24,000 (1.4% of all cancer cases), while the number of deaths in 2014 will be just over 11,000 (1.9% of all cancer cases).

In WO-A-2010/085377, the compound of formula I was shown to have excellent in vitro activity against multiple myeloma cell lines, with activities in the range of □35-100 greater than the activity shown by bendamustin.

Leukemia is a type of cancer of the blood or bone marrow characterized by an abnormal increase of immature white blood cells called "blasts". Instead of producing normal, functioning white blood cells to fight infection the body produces large numbers of these non-functional blasts. Leukemia is a broad term covering a spectrum of diseases. In turn, it is part of the even broader group of diseases affecting the blood, bone marrow and lymphoid system, which are all known as hematological neoplasms. The most common forms are acute lymphoblastic leukemia (ALL), chronic lymphocytic leukemia (CLL), acute myeloid leukemia (AML) and chronic myeloid leukemia (CML), with less common forms including hairy cell leukemia (HCL), T-cell prolymphocytic leukemia (T-PLL), large granular lymphocytic leukemia and T-cell acute lymphoblastic leukemia. It is estimated that the number of new cases in the United States in 2014 will be over 52,000 (3.1% of all new cancers in the US) with over 24,000 deaths (4.1% of all cancer deaths in the US). The percentage survival rate over five years is currently 57.2%, a figure significantly lower than for many other cancers, with the survival rate over five years for acute myeloid leukemia being particularly low at only 20%.

Lymphoma is a cancer of the lymphatic system. There are two main types of lymphoma, namely Hodgkin lymphoma and non Hodgkin lymphoma.

Non Hodgkin lymphoma is the more common form of lymphoma. The lymphatic system runs throughout the body, and it is therefore possible to find non Hodgkin lymphoma in almost all parts of the body. In patients with non Hodgkin lymphoma, some of their white blood cells (lymphocytes) divide abnormally. They do not have any resting time like normal cells and they start to divide continuously, so too many are produced. They do not naturally die off as they usually do. These cells start to divide before they are fully mature and therefore cannot fight infection as normal white blood cells do. All the abnormal lymphocytes start to collect in the lymph nodes or other places such as the bone marrow or spleen. They can then grow into tumours and begin to cause problems within the lymphatic system or the organ in which they are growing. For example, if a lymphoma starts in the thyroid gland it can affect the normal production of thyroid hormones. There are many different types of non Hodgkin lymphoma. They can be classified in several different ways. One way is by the type of cell affected. In non Hodgkin lymphoma two types of lymphocyte can be affected—B cells and T cells. This is classified as B cell lymphoma or a T cell lymphoma. Most people with non Hodgkin lymphoma have B cell lymphomas. T cell lymphomas are more common in teenagers and young adults.

The cells of Hodgkin lymphoma have a particular appearance under the microscope. These cells are called Reed Sternberg cells. Non Hodgkin lymphomas do not have Reed Sternberg cells. It is important for doctors to be able to tell the difference between Hodgkin lymphoma and non Hodgkin lymphoma cells as they are two different diseases. In Hodgkin lymphoma, it is cells in the lymph nodes that have become cancerous.

The % survival rate over 5 years in 2009 for patients with non Hodgkin lymphoma was 63%, while the survival rate for those with Hodgkin lymphoma over the same period was 83%.

Breast cancer is a cancer that forms in tissues of the breast. The most common type of breast cancer is ductal carcinoma, which begins in the lining of the milk ducts (thin tubes that carry milk from the lobules of the breast to the nipple). Another type of breast cancer is lobular carcinoma, which begins in the lobules (milk glands) of the breast. Breast cancers can be classified into sub-groups as claudin-low tumors, basal-like tumors, human epidermal growth factor receptor 2 (HER2) positive tumors, luminal A tumors and luminal B tumors. Invasive breast cancer is breast cancer that has spread from where it began in the breast ducts or lobules to surrounding normal tissue. Breast cancer occurs in both men and women, although male breast cancer is rare. In 2014, it is estimated that there will be nearly 233,00 new cases in women and 2,400 in men, with 40,00 female deaths and just over 400 male deaths.

Approximately 15 out of every 100 women with breast cancer have triple-negative breast cancer, i.e. are estrogen negative, are progesterone negative and are HER2 negative. Recurrent triple-negative breast cancer is a condition of high unmet medical need, due to its aggressive biology, fast development of drug resistance and lack of molecular targets. Until now, chemotherapy remains the standard of care for advanced triple-negative breast cancer with a poor median overall survival. In WO-A-2010/085377, the compound of formula I below is disclosed. It is a first-in-class dual-functional alkylating-HDACi fusion molecule which potently inhibits the HDAC pathway.

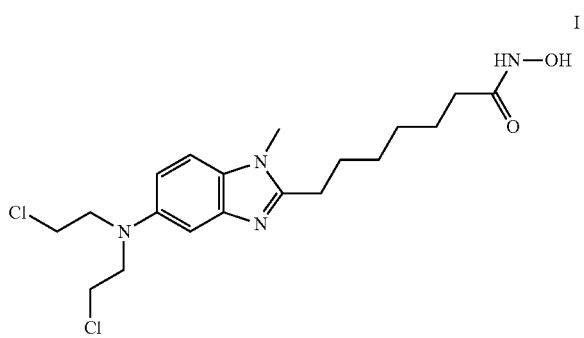 [SMILES: Cn1c(CCCCCCC(=O)NO)nc2cc(N(CCCl)CCCl)ccc21]

I

Biological assays showed that the compound of formula I potently inhibits HDAC enzyme (HDAC1 $IC_{50}$ of 9 nM) and it has been shown to have excellent in vitro activity against multiple myeloma cell lines.

There is a need for more effective cancer treatments, including the treatment of breast cancer and of hematologic cancers such as multiple myeloma, lymphoma or leukemia. Currently, these conditions affect many people and the medium to long-term prognosis is not good for many of these conditions.

SUMMARY OF THE INVENTION

In a first aspect of the present invention there is provided a combination comprising a class III receptor tyrosine kinase inhibitor and a compound of formula I or a pharmaceutically acceptable salt thereof:

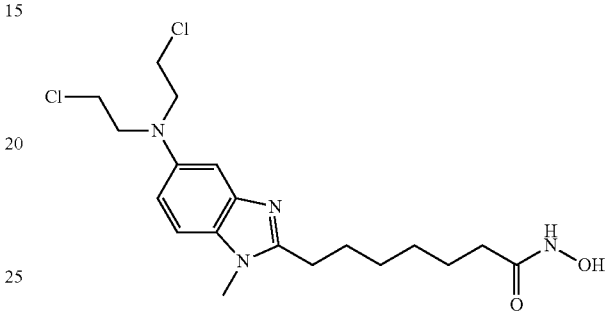

I

We have found that combinations of a compound of formula I or a pharmaceutically acceptable salt thereof and a class III receptor tyrosine kinase inhibitor such as quizartinib are particularly effective in the treatment of cancers such as hematologic cancers (e.g. leukemia, lymphoma and multiple myeloma) and breast cancer, such that they are highly promising in efforts to address the problem of finding more effective treatments for cancer.

In a second aspect of the present invention, there is provided a pharmaceutical composition comprising a pharmaceutically acceptable diluent or carrier and a combination according to the first aspect of the invention.

In a third aspect of the present invention, there is provided a kit comprising a combination according to the first aspect of the present invention and, optionally, instructions for treating a patient.

In a fourth aspect of the present invention, there is provided a combination, composition or kit according to the first, second or third aspect of the present invention for use in the treatment of cancer, such as hematologic cancers and breast cancer.

In a fifth aspect of the present invention, there is provided a method of treating cancer in a patient in need thereof comprising administering to said patient a combination, composition or kit according to the first, second or third aspect of the present invention.

DETAILED DESCRIPTION OF THE INVENTION

Figure 1:
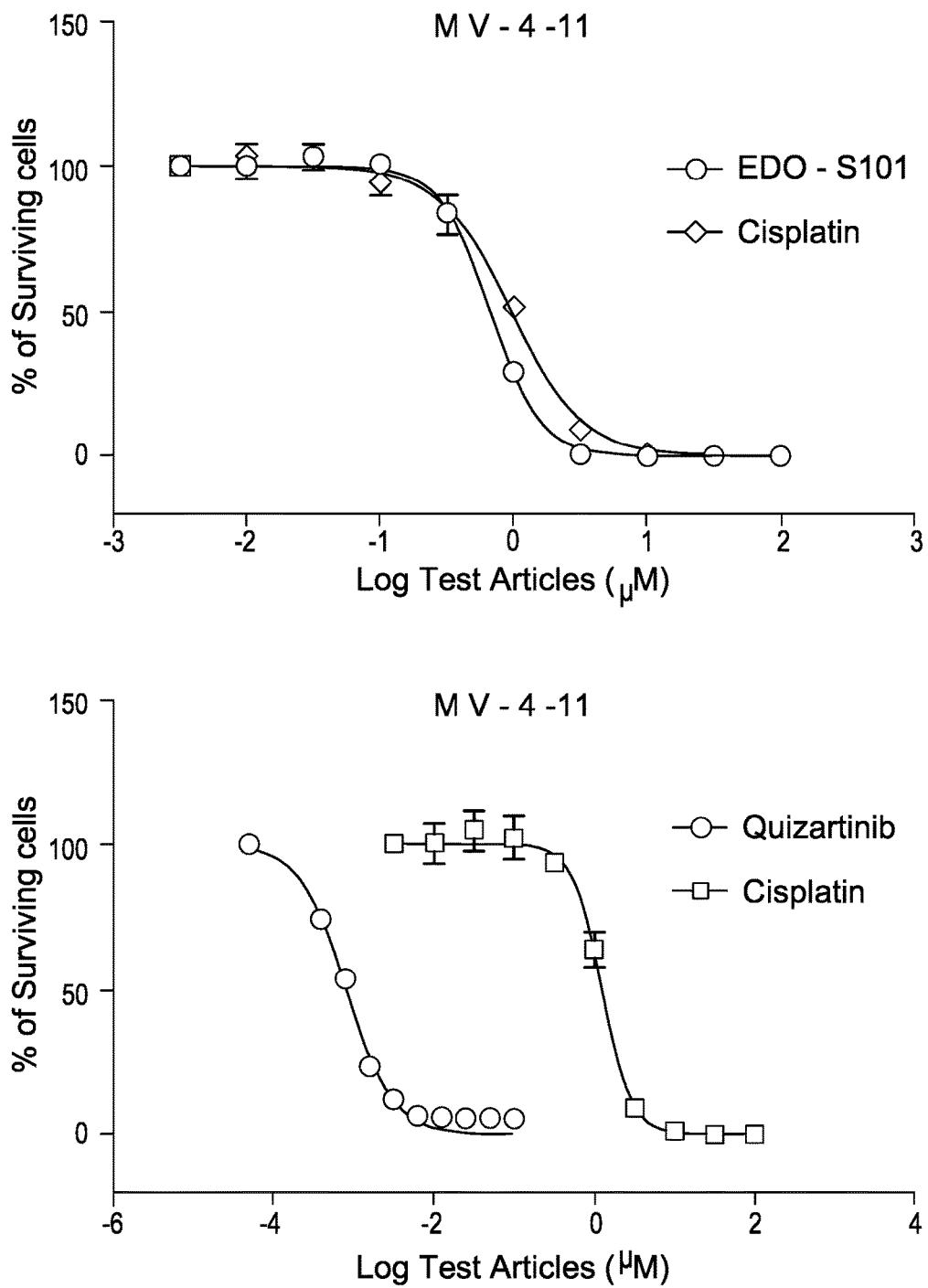
FIG. 1 is a plot of the % surviving in vitro MV-4-11 acute myeloid leukemia cells as a % of control versus log 1050 for each of the tested compounds in single compound tests (EDO-S101 versus cisplatin and quizartinib versus cisplatin)

In the present application, a number of general terms and phrases are used, which should be interpreted as follows.

"Animal" includes humans, non-human mammals (e.g., dogs, cats, rabbits, cattle, horses, sheep, goats, swine, deer, and the like) and non-mammals (e.g., birds, and the like).

"Pharmaceutically acceptable salts" means salts of compounds of the present invention which are pharmaceutically acceptable, as defined above, and which possess the desired pharmacological activity. Such salts include acid addition salts formed with inorganic acids, or with organic acids. Pharmaceutically acceptable salts also include base addition salts which may be formed when acidic protons present are capable of reacting with inorganic or organic bases. Generally, such salts are, for example, prepared by reacting the free acid or base forms of these compounds with a stoichiometric amount of the appropriate base or acid in water or in an organic solvent or in a mixture of the two. Generally, non-aqueous media like ether, ethyl acetate, ethanol, isopropanol or acetonitrile are preferred. Examples of the acid addition salts include mineral acid addition salts such as, for example, hydrochloride, hydrobromide, hydroiodide, sulfate, bisulfate, sulfamate, nitrate, phosphate, and organic acid addition salts such as, for example, acetate, trifluoroacetate, maleate, fumarate, citrate, oxalate, succinate, tartrate, salicylate, tosylate, lactate, naphthalenesulphonae, malate, mandelate, methanesulfonate and p-toluenesulfonate. Examples of the alkali addition salts include inorganic salts such as, for example, sodium, potassium, calcium and ammonium salts, and organic alkali salts such as, for example, ethylenediamine, ethanolamine, N,N-dialkylenethanolamine, triethanolamine and basic aminoacids salts.

It has surprisingly been discovered that combinations of a compound of formula I or a pharmaceutically acceptable salt thereof and a class III receptor tyrosine kinase inhibitor such as quizartinib are particularly effective in the treatment of cancers including hematologic cancers such as multiple myeloma, leukemia and lymphoma, and breast cancer such that they are highly promising in efforts to address the problem of finding more effective treatments for cancer.

In the combination of the present invention, the pharmaceutically acceptable salt of the compound of formula I may preferably be the hydrochloride, hydrobromide, hydroiodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate or acetate, and more preferably the acetate.

In the combination of the present invention, the class III receptor tyrosine kinase inhibitor is preferably an inhibitor of a class III tyrosinse receptor kinase selected from FMS-related tyrosine kinase 3 (FLT3/STK1), colony-stimulating factor 1 receptor (CSF-1R), stem cell factor receptor (SCFR) and platelet derived growth factor receptors (PDGFRs).

Preferably, the class III receptor tyrosine kinase inhibitor is an FMS-related tyrosine kinase 3 (FLT3) inhibitor selected from the group consisting of quizartinib, sunitinib, linifanib, foretinib, staurosporine and tandutinib, and more preferably it is quizartinib.

In a further preferred combination of the present invention comprising a compound of formula I or a pharmaceutically acceptable salt thereof and a class III receptor tyrosine kinase inhibitor, said combination may further comprise one or more additional pharmaceutically active agents. Particularly suitable pharmaceutically active agents are anti-tumor agents having a different mode of action to the compound of formula I or a pharmaceutically acceptable salt thereof and the class III receptor tyrosine kinase inhibitor, e.g. alkylating agents such as nitrosureas, ethylenimines, alkylsulfonates, hydrazines and triazines, and platinum based agents; plant alkaloids, taxanes, vinca alkaloids; anti-tumor antibiotics such as chromomycins, anthracyclines, and miscellaneous antibiotics such as Mitomycin and Bleomycin; anti-metabolites such as folic acid antagonists, pyrimidine antagonists, purine antagonists and adenosine deaminase inhibitors; glucocorticoids such as dexamethasone; proteasome inhibitors such as bortezomib and carfilzomib, topoisomerase inhibitors such as topoisomerase I inhibitors, topoisomerase II inhibitors, miscellaneous anti-neoplastics such as ribonucleotide reductase inhibitors, adrenocortical steroid inhibitor, anti-microtubule agents, and retinoids; protein kinases; heat shock proteins, poly-ADP (adenosine diphosphate)-ribose polymerase (PARP), hypoxia-inducible factors (HIF), proteasome, Wnt/Hedgehog/Notch signaling proteins, TNF-alpha, matrix metalloproteinase, farnesyl transferase, apoptosis pathway, histone deacetylases (HDAC), histone acetyltransferases (HAT), and methyltransferase; hormonal therapies, vascular disrupting agent, gene therapy, RNAi cancer therapy, chemoprotective agents, antibody conjugate, cancer immunotherapy such as Interleukin-2, cancer vaccines or monoclonal antibodies; and preferably DNA damaging agents, anti-metabolites, topoisomerase inhibitors, anti-microtubule agents, glucocorticoids, proteasome inhibitors, EGFR inhibitors, HER2 inhibitors, VEGFR2 inhibitors, BRAF inhibitors, Bcr-Abl inhibitors, PDGFR inhibitors, ALK inhibitors, PLK inhibitors, MET inhibitors, epigenetic agents, HSP90 inhibitors, PARP inhibitors, CHK inhibitors, aromatase inhibitor, estrogen receptor antagonist, and antibodies targeting VEGF, HER2, EGFR, CD50, CD20, CD30, CD33, etc.

In one embodiment of the combination of the present invention the compound of formula I or a pharmaceutically acceptable salt thereof and the class III receptor tyrosine kinase inhibitor of the combination are adapted for administration concurrently, sequentially or separately. Preferably, the compound of formula I or a pharmaceutically acceptable salt thereof and the class III receptor tyrosine kinase inhibitor of the combination are adapted for administration concurrently.

In one embodiment of the combination of the present invention, the class III receptor tyrosine kinase inhibitor is quizartinib and the compound of formula I or a pharmaceutically acceptable salt thereof is

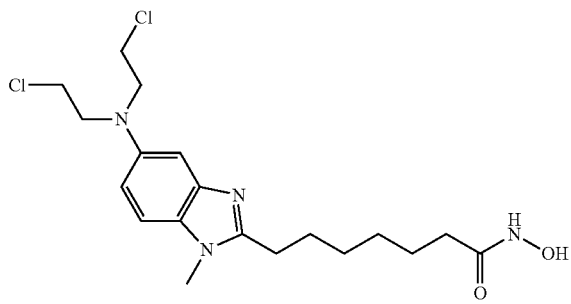

or the acetate salt thereof.

The molar ratio of the class III receptor tyrosine kinase inhibitor to the compound of formula I or a pharmaceutically acceptable salt thereof in the combination of the present invention is typically from 1:2000 to 2000:1. Preferably, the molar ratio of class III receptor tyrosine kinase inhibitor to compound of formula I or a pharmaceutically acceptable salt thereof in said combination is from 1:2000 to 1:100, more preferably the molar ratio of class III receptor tyrosine kinase inhibitor to compound of formula I or a pharmaceutically acceptable salt thereof in said combination is from 1:1000 to 1:500, and most preferably it is from 1:900 to 1:500, e.g. 1:900, 1:800, 1:700, 1:600 or 1:500.

One particularly preferred combination of the present invention comprises the compound of formula I or the acetate salt thereof and quizartinib, wherein the molar ratio of the quizartinib to the compound of formula I or the acetate salt thereof in said combination is from 1:900 to 1:500, e.g. 1:900, 1:800, 1:700, 1:600 or 1:500.

It has been surprisingly found that many of the combinations comprising quizartinib and a compound of formula I or a pharmaceutically acceptable salt thereof are synergistic combinations. In other words, the potency of the combinations has been measured with the Calcusyn software (biosoft, Ferguson, Mo., USA), which is based on the Chou Talay method (Chou et al., *Adv. Enzyme Regul.*, 22, 27-55 (1984)), that calculates a combination index (CI) with the following interpretation:

CI >1: antagonist effect, CI=1: additive effect and CI<1 synergistic effect.

For many of the dual combinations of the invention comprising quizartinib and a compound of formula I or a pharmaceutically acceptable salt, CI has been found to be less than 1, indicating synergy.

The pharmaceutical composition according to the second aspect of the present invention comprises a pharmaceutically acceptable diluent or carrier and a combination according to the first aspect of the present invention. Preferred compositions of the second invention include those comprising the preferred combinations of the present invention as described and exemplified above.

The pharmaceutically acceptable diluent or carrier of the pharmaceutical composition according to the second aspect of the present can be any suitable dispersant, excipient, adjuvant, or other material which acts as a carrier for the active agents of the combination of the present invention and which does not interfere with the active agents present in said combination. Examples of typical pharmaceutically acceptable carriers and diluents may be found in "Remington's Pharmaceutical Sciences" by E. W. Martin and these include water, saline, dextrose solution, serum solution, Ringer's solution, polyethylene glycol (e.g PEG400), a surfactant (e.g Cremophor), a cyclopolysaccharide (e.g hydroxypropyl-β-cyclodextrin or sulfobutyl ether β-cyclodextrins), a polymer, a liposome, a micelle, a nanosphere, etc.

In the third aspect of the present invention, there is provided a kit comprising a combination according to the first aspect of the present invention and, optionally, instructions for treating a patient. Typically, a kit can comprise a compound of formula I or pharmaceutically acceptable salt thereof and a class III receptor tyrosine kinase inhibitor together with instructions for treating a patient. Each active agent can be provided in a suitable container. The kit may further comprise a delivery system, e.g. for the compound of formula I or pharmaceutically acceptable salt thereof and a class III receptor tyrosine kinase inhibitor or a combination thereof.

The instructions may advise administering the class III receptor tyrosine kinase inhibitor and the compound of formula I or a pharmaceutically acceptable salt thereof concurrently, sequentially or separately according to variables such as the specific condition being treated, the state of that condition, the activity of the specific compounds employed; the specific combination employed; the age, body weight, general health, sex and diet of the patient; the time of administration, route of administration, and rate of excretion of the specific compounds employed; the duration of the treatment; drugs used in combination or contemporaneously with the specific compounds employed; and like factors well known in the medical arts.

Preferred kits according to the third aspect of the present invention include those comprising the preferred combinations of the present invention as described and exemplified above.

In the fourth aspect of the present invention, there is provided the combination, composition or kit according to the first, second or third aspect of the present invention for use in the treatment of cancer.

In the fifth aspect of the present invention, there is provided a method of treating cancer in a patient in need thereof comprising administering to said patient the combination, composition or kit according to the first, second or third aspect of the present invention.

It has been found that the combinations, compositions and kits of the present invention are highly active both in vitro and in vivo against a wide variety of tumour cell types. The anti-tumour activity shown by these double combinations of the present invention, and by the combinations in the compositions and kits of the present invention is, in many cases, more than merely additive, showing combination indexes CI of significantly less than 1, indicating synergy for these combinations. This surprising finding is a further support for the particular effectiveness of the combinations, compositions and kits of the present invention in the treatment of cancer.

Examples of cancers which are treatable by the combinations, compositions and kits of the present invention include hematologic cancers such as multiple myeloma, lymphoma and leukemia, breast cancer, lung cancer, colorectal cancer, prostate cancer, testicular cancer, pancreatic cancer, liver cancer, stomach cancer, biliary tract cancer, esophageal cancer, gastrointestinal stromal tumor, cervical cancer, ovarian cancer, uterine cancer, renal cancer, melanoma, basal cell carcinoma, squamous cell carcinoma, bladder cancer, sarcoma, mesothelioma, thymoma, myelodysplastic syndrome, glioblastoma and myeloproliferative disease. In particular, the combinations, compositions and kits of the present invention are effective against hematologic cancer such as multiple myeloma, lymphoma and leukemia, and breast cancer.

In one embodiment of the combination, composition or kit for use in the treatment of a cancer according to the fourth aspect of the present invention or the method of treatment according to the fifth aspect of the present invention, the cancer is selected from a hematologic cancer and breast cancer.

Where the combination, composition or kit of the present invention is for use in the treatment of a hematologic cancer, this may preferably be selected from multiple myeloma (e.g. active myeloma, plasmacytoma, light chain myeloma or non-secretory myeloma), lymphoma (e.g. Hodgkin lymphoma or non-Hodgkin lymphoma) and leukemia [acute lymphoblastic leukemia (ALL), chronic lymphocytic leukemia (CLL), acute myeloid leukemia (AML, including myeloblastic leukemia, acute promyelocytic leukemia, acute myelomonocytic leukemia, acute monocytic leukemia, acute erythroleukemia and acute megakaryotic leukemia, with all forms being treatable in all phases including relapsed and refractory phases), chronic myeloid leukemia (CML), hairy cell leukemia (HCL), T-cell prolymphocytic leukemia (T-PLL), large granular lymphocytic leukemia or T-cell acute lymphoblastic leukemia]. The combination for use in the treatment of acute myeloid leukemia (AML) is particularly preferred.

Where the combination, composition or kit of the present invention is for use in the treatment of breast cancer, the breast cancer may typically be selected from claudin-low tumors, basal-like tumors, human epidermal growth factor receptor 2 (HER2) positive tumors, luminal A tumors and luminal B tumors, and it is preferably a triple-negative breast cancer.

In one preferred embodiment of the combination, composition or kit for use in the treatment of cancer according to the present invention and the method of treatment of cancer according to the present invention, the class III receptor tyrosine kinase inhibitor and the compound of formula I or a pharmaceutically acceptable salt thereof are administered concurrently, sequentially or separately. More preferably, the class III receptor tyrosine kinase inhibitor and the compound of formula I or a pharmaceutically acceptable salt thereof are administered concurrently.

In the combination, composition or kit for use in the treatment of cancer and the method of treatment of cancer in accordance with the present invention, the compound of formula I or a pharmaceutically acceptable salt thereof is typically administered to the patient in need thereof at a dosage range of 10 to 100 mg/kg body weight patient, and preferably at a dosage range of 40 to 80 mg/kg body weight. Typically, the class III receptor tyrosine kinase inhibitor is administered at a dosage range of from 0.01 to 1 mg/kg body weight patient, and preferably, it is administered at a dosage range of from 0.1 to 0.25 mg/kg body weight patient.

The therapeutically effective amount of a combination, composition or kit according to the present invention is an amount of the combination, composition or kit which confers a therapeutic effect in accordance with the fourth and fifth aspects of the present invention on the treated subject, at a reasonable benefit/risk ratio applicable to any medical treatment. The therapeutic effect may be objective (i.e. measurable by some test or marker) or subjective (i.e. subject gives an indication of or feels an effect). An effective amount of the combination, composition or kit according to the present invention is believed to be one wherein the compound of formula I or a salt thereof is included in the combination at a dosage range of from 10 to 100 mg/kg body weight patient (e.g. 40 to 80 mg/kg body weight such as 40, 50, 60, 70 or 80 mg/kg body weight) and the class III receptor tyrosine kinase inhibitor is administered at a dosage range of from 0.1 to 0.25 mg/kg body weight patient (e.g. 0.1, 0.15, 0.2 or 0.25 mg/kg body weight patient).

Effective doses will vary depending on route of administration, as well as the possibility of co-usage with other active agents. It will be understood, however, that the total daily usage of the combinations, compositions and kits of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The present invention is also directed to the use of a combination, composition or kit according to the first, second or third aspect of the present invention in the manufacture of a medicament for the treatment of cancer, e.g. for the treatment of a hematologic cancer or breast cancer.

Suitable examples of the administration form of the combination, composition or kit of the present invention include without limitation oral, topical, parenteral, sublingual, rectal, vaginal, ocular, and intranasal. Parenteral administration includes subcutaneous injections, intravenous, intramuscular, intrasternal injection or infusion techniques. Preferably, the combinations, compositions and kits are administered parenterally. Combinations, compositions and kits of the invention can be formulated so as to allow a combination or composition of the present invention to be bioavailable upon administration of the combination, composition or kit to an animal, preferably human. Compositions can take the form of one or more dosage units, where for example, a tablet can be a single dosage unit, and a container of a combination or composition of the present invention in aerosol form can hold a plurality of dosage units.

Preferably the combinations of the present invention are provided in the form of kits. Typically, a kit includes a compound of formula I or a pharmaceutically acceptable salt thereof and a class III receptor tyrosine kinase inhibitor. In certain embodiments, a kit can include one or more delivery systems, e.g. the class III receptor tyrosine kinase inhibitor, the compound of formula I or a pharmaceutically acceptable salt thereof, or a combination thereof, and directions for the use of the kit (e.g. instructions for treating a subject). These directions/instructions may advise administering the class III receptor tyrosine kinase inhibitor and the compound of formula I or a pharmaceutically acceptable salt thereof of the combination concurrently, sequentially or separately according to variables such as the specific condition being treated, the state of that condition, the activity of the specific compounds employed; the specific combination employed; the age, body weight, general health, sex and diet of the patient; the time of administration, route of administration, and rate of excretion of the specific compounds employed; the duration of the treatment; drugs used in combination or contemporaneously with the specific compounds employed; and like factors well known in the medical arts.

The pharmaceutically acceptable diluent or carrier can be particulate, so that the compositions are, for example, in tablet or powder form. The carrier(s) can be liquid, with the combinations, compositions or kits being, for example, an oral syrup or injectable liquid. In addition, the carrier(s) can be gaseous, so as to provide an aerosol composition useful in, for example, inhalatory administration. Such pharmaceutical carriers can be liquids, such as water and oils, including those of petroleum, animal, vegetable or synthetic origin, such as peanut oil, soybean oil, mineral oil, sesame oil and the like. The carriers can be saline, gum acacia, gelatin, starch paste, talc, keratin, colloidal silica, urea, and the like. In addition, auxiliary, stabilizing, thickening, lubricating and coloring agents can be used. In one embodiment, when administered to an animal, the combination, composition or kit of the present invention and the pharmaceutically acceptable carriers are sterile. Water is a preferred carrier when the combination, composition or kit of the present invention is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

When intended for oral administration, the combination, composition or kit may be in solid or liquid form, where semi-solid, semi-liquid, suspension and gel forms are included within the forms considered herein as either solid or liquid.

As a solid composition for oral administration, the combination, composition or kit can be formulated into a powder, granule, compressed tablet, pill, capsule, chewing gum, wafer or the like form. Such a solid composition typically contains one or more inert diluents, either as a single tablet comprising all active agents or as a number of separate solid compositions, each comprising a single active agent of the combination of the present invention (in the case of the kit). In addition, one or more of the following can be present: binders such as carboxymethylcellulose, ethyl cellulose, microcrystalline cellulose, or gelatin; excipients such as starch, lactose or dextrins, disintegrating agents such as alginic acid, sodium alginate, corn starch and the like; lubricants such as magnesium stearate; glidants such as colloidal silicon dioxide; sweetening agents such as sucrose or saccharin; a flavoring agent such as peppermint, methyl salicylate or orange flavoring; and a coloring agent.

When the combination, composition or kit is in the form of a capsule (e. g. a gelatin capsule), it can contain, in addition to materials of the above type, a liquid carrier such as polyethylene glycol, cyclodextrin or a fatty oil.

The combination, composition or kit can be in the form of a liquid, e. g. an elixir, syrup, solution, emulsion or suspension. The liquid can be useful for oral administration or for delivery by injection. When intended for oral administration, a combination, composition or kit can comprise one or more of a sweetening agent, preservatives, dye/colorant and flavor enhancer. In a combination or composition for administration by injection, one or more of a surfactant, preservative, wetting agent, dispersing agent, suspending agent, buffer, stabilizer and isotonic agent can also be included.

The preferred route of administration is parenteral administration including, but not limited to, intradermal, intramuscular, intraperitoneal, intravenous, subcutaneous, intranasal, epidural, intranasal, intracerebral, intraventricular, intrathecal, intravaginal or transdermal. The preferred mode of administration is left to the discretion of the practitioner, and will depend in part upon the site of the medical condition (such as the site of cancer). In a more preferred embodiment, the present combinations, compositions and kits of the present invention are administered intravenously.

The liquid combinations and compositions of the invention, whether they are solutions, suspensions or other like form, can also include one or more of the following: sterile diluents such as water for injection, saline solution, preferably physiological saline, Ringer's solution, isotonic sodium chloride, fixed oils such as synthetic mono or digylcerides, polyethylene glycols, glycerin, or other solvents; antibacterial agents such as benzyl alcohol or methyl paraben; and agents for the adjustment of tonicity such as sodium chloride or dextrose. A parenteral combination or composition can be enclosed in an ampoule, a disposable syringe or a multiple-dose vial made of glass, plastic or other material. Physiological saline is a preferred adjuvant.

For administration (e.g. intravenous) the combination or composition may typically comprise the compound of formula I or a salt thereof at a dosage range of from 10 to 100 mg/kg body weight patient and preferably from 40 to 80 mg/kg body weight patient. Typically, the combination or composition may comprise the class III receptor tyrosine kinase inhibitor at a dosage range of from 0.1 to 1 mg/kg body weight patient, and preferably of from 0.1 to 0.25 mg/kg body weight patient.

The combinations of the inventions may be formulated such that the class III receptor tyrosine kinase inhibitor and the compound of formula I or a pharmaceutically acceptable salt thereof of the combination are adapted for administration concurrently, sequentially or separately. Preferably, they are administered concurrently.

The combination, composition or kit of the present invention can be administered by any convenient route, for example by infusion or bolus injection, by absorption through epithelial or mucocutaneous linings.

In specific embodiments, it can be desirable to administer one or more combinations, compositions or kits of the present invention or combinations, compositions or kits locally to the area in need of treatment. In one embodiment, administration can be by direct injection at the site (or former site) of a cancer, tumor or neoplastic or pre-neoplastic tissue.

Pulmonary administration can also be employed, e. g. by use of an inhaler or nebulizer, and formulation with an aerosolizing agent, or via perfusion in a fluorocarbon or synthetic pulmonary surfactant. In certain embodiments, the combination, composition or kit of the present invention or compositions can be formulated as a suppository, with traditional binders and carriers such as triglycerides.

The present combination, composition or kit can take the form of solutions, suspensions, emulsion, tablets, pills, pellets, capsules, capsules containing liquids, powders, sustained-release formulations, suppositories, emulsions, aerosols, sprays, suspensions, or any other form suitable for use. Other examples of suitable pharmaceutical carriers are described in "Remington's Pharmaceutical Sciences" by E. W. Martin.

The pharmaceutical combinations, compositions or kits can be prepared using methodology well known in the pharmaceutical art. For example, a composition intended to be administered by injection can be prepared by combining a combination or composition of the present invention with water so as to form a solution. A surfactant can be added to facilitate the formation of a homogeneous solution or suspension.

The combinations, compositions and kits of the present invention are particularly effective in the treatment of cancer. It has been shown that the combinations, compositions and kits of the present invention are highly active both in vitro and in vivo against a wide variety of tumour cell types making them particularly interesting for development for use in the treatment of cancer, e.g. hematologic cancer and breast cancer.

EXAMPLES

In the following examples, the compound having the following formula I is referred to as EDO-S101.

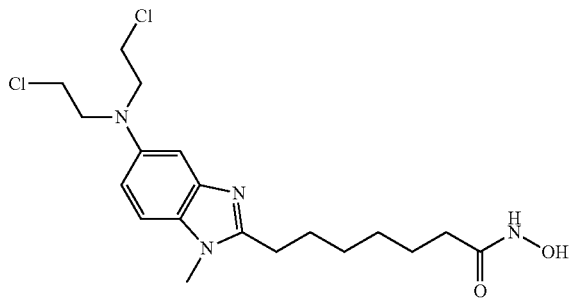

I

Example 1 EDO-S101 Combinations In Vitro—Acute Myeloid Leukemia Cell Line MV-4-11

The acute myeloid leukemia cell line MV-4-11 (obtained from the ATCC) was cultured in media supplemented with 10% fetal bovine serum (FBS) at a temperature of 37° C., 5% $CO_2$ and 95% humidity. Culture media was purchased from GIBCO, USA. The cells were plated out in 96-Well Flat Clear Bottom Black Polystyrene TC-Treated Microplates (Cat#3603, Corning®).

The compounds tested were EDO-S101 and quizartinib, as well as the reference control cisplatin. Equipment used was the EnVision Multi Label Reader, PerkinElmer (USA). $CO_2$ Water Jacketed Incubator, Therma (USA). Reverse microscope, Chongguang XDS-1B, Chongqing Guangdian Corp. (Chongqing, P.R.China).

The cells were harvested respectively during the logarithmic growth period and counted with a hemocytometer. The cell viability is over 98% by trypan blue exclusion.

For single drug testing, the cell concentrations were adjusted to $4.44 \times 10^4$ cells/ml with the medium supplemented with 10% FBS. 90 µl cell suspensions were added to 96-well plates, such that the final cell density was $4 \times 10^3$ cells/well. The appropriate cell density was determined and adjusted according to the results of our first test.

The next day, 10 µl (10×) of drug solution was prepared and dispensed in each well (triplicate for each drug concentration). After 72 h incubation, 100 µl CellTiter-Glo® Reagent was added to each well. The contents were mixed for 2 minutes on an orbital shaker to induce cell lysis. The plate was allowed to incubate at room temperature for 10 minutes to stabilize the luminescent signal. Finally, the luminescence was recorded using an EnVision Multi Label Reader.

For two drug combination testing, the cell concentrations were adjusted to $5.00 \times 10^4$/ml with the medium supplemented with 10% FBS. 80 µl cell suspensions were added to 96-well plates, such that the final cell densities were $4 \times 10^3$ cells/well. The appropriate cell density was determined and adjusted according to the results of our first test.

The next day, 10 µl (10×) of each drug solution was prepared and dispense in each well simultaneously (triplicate for each concentration). After 72 h incubation, 100 µL CELLTITER-GLO® Reagent was added to each well. The contents were mixed for 2 minutes on an orbital shaker to induce cell lysis. The plate was allowed to incubate at room temperature for 10 minutes to stabilize luminescent signal. Then the luminescence was recorded using EnVision Multi Label Reader.

The data were displayed graphically using GraphPad Prism 5.0. In order to calculate $IC_{50}$, a dose-responsive curve was fitted using nonlinear regression model with a sigmoidal dose response. The formula of surviving rate is shown below, and the $IC_{50}$ was automatically produced by GraphPad Prism 5.0.

The surviving rate (%)=$(Lum_{Test\ article}-LUM_{Medium\ control})/(LUM_{None\ treated}-LUM_{Medium\ control}) \times 100\%$.

Compound interactions were calculated by multiple drug effect analysis and performed by the median equation principle with CalcuSyn software from the mean affected fraction at each drug ratio concentration of each drug according to the methodology described by Chou and Talalay (Chou et al., Adv. Enzyme Regul., 22, 27-55 (1984)), that calculates a combination index (CI) with the following interpretation:

CI>1: antagonist effect, CI=1: additive effect and CI<1 synergistic effect.

The CI was calculated from the mean affected fraction at each drug ratio concentration of each drug.

Figure 2:
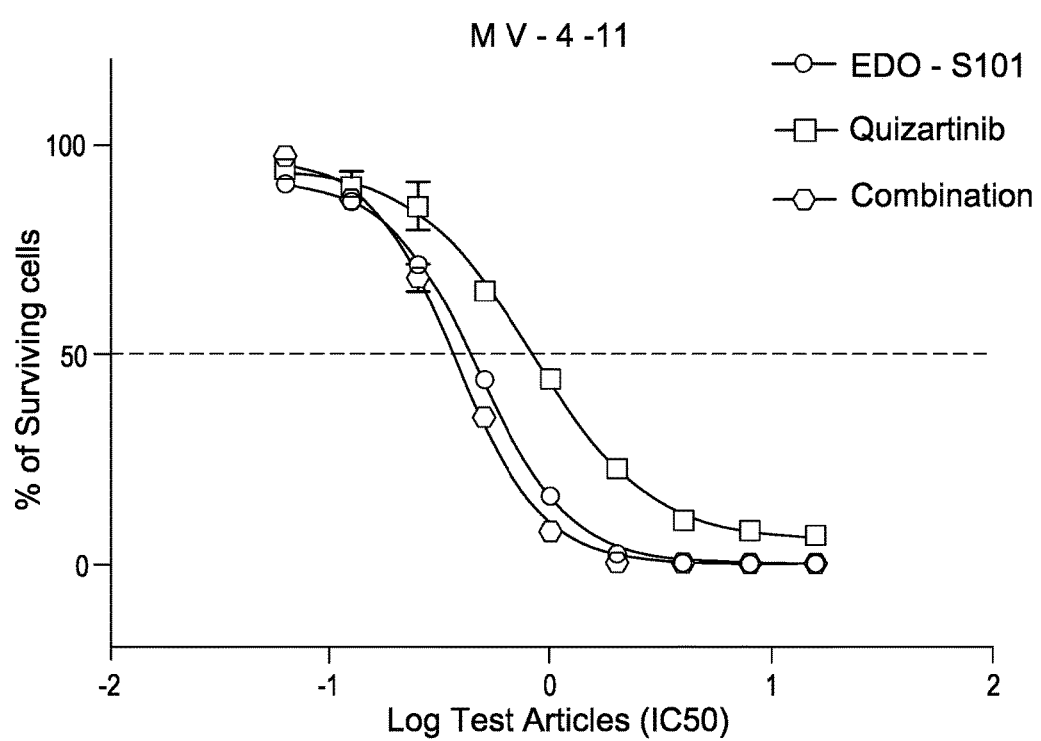
FIG. 2 is a plot of the % surviving in vitro MV-4-11 acute myeloid leukemia cells as a % of control versus log 1050 for each of the tested compounds in single compound tests and also for the combination (EDO-S101, quizartinib and the combination thereof)

In the plots of % surviving cells versus log concentration of test drugs in FIG. 1 (single drug tests), the $IC_{50}$ values for the control cisplatin and EDO-S101 were 0.9607 and 0.6675 respectively, while those for quizartinib and cisplatin were 0.0008043 and 1.256 respectively. FIG. 2, showing a plot of % surviving cells versus log $IC_{50}$ tested drug shows excellent combined activity for the EDO-S101 and quizartinib combination. This is confirmed in the CI values in Table 1 below:

TABLE 1

| Drug | Combination ratio | CI Values at | | | DRI values at | | |
|---|---|---|---|---|---|---|---|
| | | ED50 | ED75 | ED90 | ED50 | ED75 | ED90 |
| EDO-S101 + Quizartinib | 1:0.00120494 | 1.07686 | 0.89385 | 0.76789 | 1.263 3.511 | 1.368 6.146 | 1.482 10.760 |

As can be seen from the CI values, the combination of EDO-S101 and quizartinib shows synergy in its activity against the acute myeloid leukemia MV-4-11 cell line.

Example 2 EDO-S101 Combinations In Vitro—Acute Myeloid Leukemia Cell Line MOLM-13

The acute myeloid leukemia cell line MOLM-13 (obtained from the ATCC) was cultured in media supplemented with 10% FBS at a temperature of 37° C., 5% $CO_2$ and 95% humidity. Culture media was purchased from GIBCO, USA. The cells were plated out in 96-Well Flat Clear Bottom Black Polystyrene TO-Treated Microplates (Cat#3603, Corning®).

The compounds tested were EDO-S101 and quizartinib, as well as the reference control cisplatin. Equipment used was the EnVision Multi Label Reader, PerkinElmer (USA). $CO_2$ Water Jacketed Incubator, Therma (USA). Reverse microscope, Chongguang XDS-1B, Chongqing Guangdian Corp. (Chongqing, P.R.China).

The cells were harvested respectively during the logarithmic growth period and counted with a hemocytometer. The cell viability is over 98% by trypan blue exclusion.

For single drug testing, the cell concentrations were adjusted to $4.44 \times 10^4$ cells/ml with the medium supplemented with 10% FBS. 90 μl cell suspensions were added to 96-well plates, such that the final cell density was $4 \times 10^3$ cells/well. The appropriate cell density was determined and adjusted according to the results of our first test.

The next day, 10 μl (10×) of drug solution was prepared and dispensed in each well (triplicate for each drug concentration). After 72 h incubation, 100 μl CellTiter-Glow Reagent was added to each well. The contents were mixed for 2 minutes on an orbital shaker to induce cell lysis. The plate was allowed to incubate at room temperature for 10 minutes to stabilize the luminescent signal. Finally, the luminescence was recorded using an EnVision Multi Label Reader.

For two drug combination testing, the cell concentrations were adjusted to $5.00 \times 10^4$/ml with the medium supplemented with 10% FBS. 80 μl cell suspensions were added to 96-well plates, such that the final cell densities were $4 \times 10^3$ cells/well. The appropriate cell density was determined and adjusted according to the results of our first test.

The next day, 10 μl (10×) of each drug solution was prepared and dispense in each well simultaneously (triplicate for each concentration). After 72 h incubation, 100 μl CellTiter-Glo® Reagent was added to each well. The contents were mixed for 2 minutes on an orbital shaker to induce cell lysis. The plate was allowed to incubate at room temperature for 10 minutes to stabilize luminescent signal. Then the luminescence was recorded using EnVision Multi Label Reader.

The data was displayed graphically using GraphPad Prism 5.0. In order to calculate $IC_{50}$, a dose-responsive curve was fitted using nonlinear regression model with a sigmoidal dose response. The formula of surviving rate is shown below, and the $IC_{50}$ was automatically produced by GraphPad Prism 5.0.

The surviving rate (%)=($Lum_{Test\ article}$−$LUM_{Medium\ control}$)/($Lum_{None\ treated}$−$LUM_{Medium\ control}$)×100%.

Compound interactions were calculated by multiple drug effect analysis and performed by the median equation principle with CalcuSyn software from the mean affected fraction at each drug ratio concentration of each drug according to the methodology described by Chou and Talalay, that calculates a combination index (CI) with the following interpretation:

CI>1: antagonist effect, CI=1: additive effect and CI<1 synergistic effect.

The CI was calculated from the mean affected fraction at each drug ratio concentration of each drug.

Figure 3:
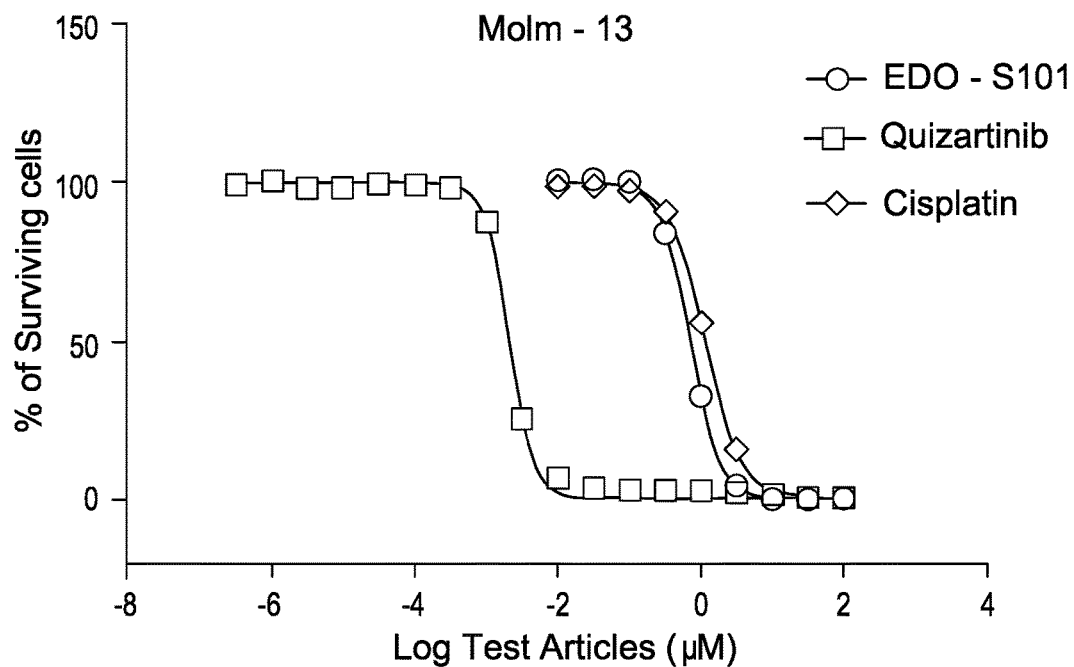
FIG. 3 is a plot of the % surviving in vitro Molm-13 acute myeloid leukemia cells as a % of control versus log 1050 for each of the tested compounds in single compound tests (EDO-S101 versus cisplatin and quizartinib and EDO-S101 versus quizartinib)
Figure 3:
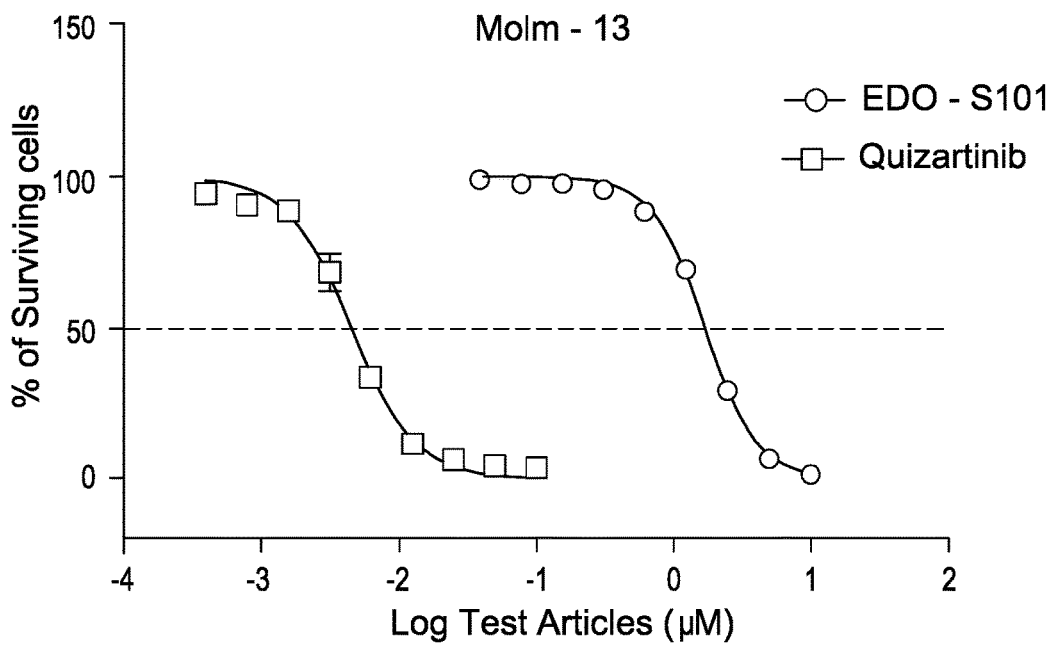

In the plots of % surviving cells versus log concentration test drugs in FIG. 3 (single drug tests), the $IC_{50}$ values for the control cisplatin, EDO-S101 and quizartinib were 1.151, and 0.7079 and 0.002112 respectively, while those for EDO-S101 and quizartinib using different doses (at 1:2 serial dilutions) were 1.720 and 0.004546 respectively.

Figure 4:
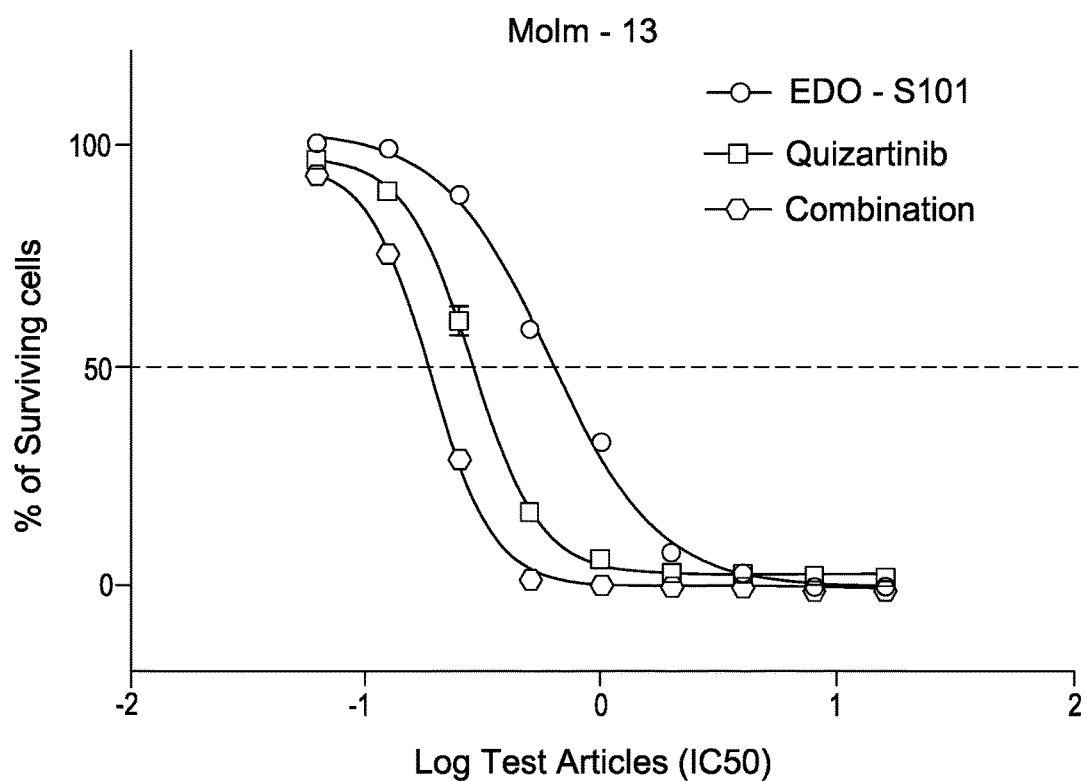
FIG. 4 is a plot of the % surviving in vitro Molm-13 acute myeloid leukemia cells as a % of control versus log IC50 for each of the tested compounds in single compound tests and also for the combination (EDO-S101, quizartinib and the combination thereof).

FIG. 4, showing a plot of % surviving cells versus log $IC_{50}$ for the tested compounds shows excellent combined activity for the EDO-S101 and quizartinib combination. This is confirmed in the CI values in Table 2 below:

TABLE 2

| Drug | Combination ratio | CI Values at | | | DRI values at | | |
| --- | --- | --- | --- | --- | --- | --- | --- |
| | | ED50 | ED75 | ED90 | ED50 | ED75 | ED90 |
| EDO-S101 + Quizartinib | 1:0.00264302 | 0.689 | 0.480 | 0.338 | 4.768 | 5.925 | 8.534 |
| | | | | | 2.087 | 3.215 | 6.645 |

As can be seen from the CI values, the combination of EDO-S101 and quizartinib shows synergy in its activity against the acute myeloid leukemia MOLM-13 cell line.

In conclusion, it can be seen that the compound of formula I (EDO-S101) show excellent activity in combination with class III receptor tyrosine kinase inhibitors such as quizartinib in acting both in vitro and in vivo against acute myeloid leukemia. Furthermore, it can be seen that the activity of these combinations is surprisingly synergistic. It is to be expected that these combinations will be active against a wide range of hematologic cancers, not just leukemia but other hematologic conditions such as lymphoma and multiple myeloma. We also believe that these combinations are likely to be active against other cancers such as breast cancer.

As a result, it is to be expected that combinations of the compound of formula I of the present invention with a class III receptor tyrosine kinase inhibitor will be of use in the treatment of cancer, particularly hematologic cancers and breast cancer.

The invention claimed is:

1. A combination comprising quizartinib and a compound of formula I or a pharmaceutically acceptable salt thereof:

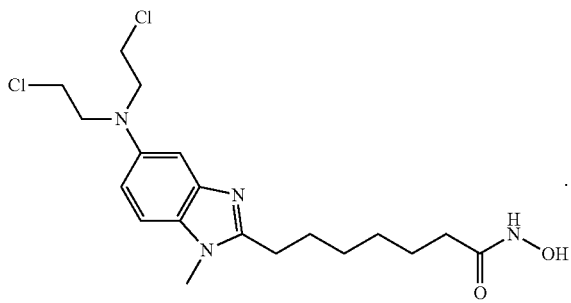

I

2. The combination according to claim 1, wherein the pharmaceutically acceptable salt of the compound of formula I is a hydrochloride, hydrobromide, hydroiodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate or acetate salt.

3. The combination according to claim 1, further comprising one or more additional pharmaceutically active agents.

4. The combination according to claim 1, wherein the compound of formula I or pharmaceutically acceptable salt thereof and quizartinib of the combination are adapted for administration concurrently, sequentially or separately.

5. The combination according to claim 1, wherein the compound of formula I or pharmaceutically acceptable salt thereof and quizartinib of the combination are adapted for administration concurrently.

6. The combination according to claim 1, wherein the molar ratio of quizartinib to the compound of formula I or pharmaceutically acceptable salt thereof in said combination is from 1:2000 to 2000:1.

7. The combination according to claim 1, wherein quizartinib and the compound of formula I or pharmaceutically acceptable salt thereof form a synergistic combination.

8. A pharmaceutical composition comprising a pharmaceutically acceptable diluent or carrier and a combination according to claim 1.

9. A kit comprising a combination according to claim 1, and optionally, instructions for treating a patient.

10. A method of treating cancer in a patient in need thereof comprising administering to said patient a combination according to claim 1.

11. The method according to claim 10, wherein said cancer is selected from a hematologic cancer and breast cancer.

12. The method according to claim 10, wherein said cancer is a hematologic cancer selected from multiple myeloma, lymphoma and leukemia.

13. The method according to claim 10, wherein said cancer is leukemia selected from acute lymphoblastic leukemia (ALL), chronic lymphocytic leukemia (CLL), acute myeloid leukemia (AML), chronic myeloid leukemia (CML), hairy cell leukemia (HCL), T-cell prolymphocytic leukemia (T-PLL), large granular lymphocytic leukemia and T-cell acute lymphoblastic leukemia.

14. The method according to claim 10, wherein said cancer is acute myeloid leukemia (AML).

15. The method according to claim 10, wherein said cancer is multiple myeloma selected from active myeloma, plasmacytoma, light chain myeloma and non-secretory myeloma.

16. The method according to claim 10, wherein said cancer is lymphoma selected from Hodgkin lymphoma and non-Hodgkin lymphoma.

17. The method according to claim 10, wherein said cancer is breast cancer selected from claudin-low tumors, basal-like tumors, human epidermal growth factor receptor 2 (HER2) positive tumors, luminal A tumors and luminal B tumors.

18. The method according to claim 10, wherein said cancer is a triple-negative breast cancer.

19. The method according to claim 10, wherein in said method the compound of formula I or pharmaceutically acceptable salt thereof and quizartinib are administered concurrently, sequentially or separately.

20. The method according to claim 10, wherein in said method the compound of formula I or pharmaceutically acceptable salt thereof and quizartinib are administered concurrently.

21. The method according to claim 10, wherein quizartinib is administered to the patient in need thereof at a dosage range of from 0.01 to 1 mg/kg body weight patient.

22. The method according to claim 10, wherein quizartinib is administered to the patient in need thereof at a dosage range of from 0.1 to 0.25 mg/kg body weight patient.

* * * * *